(12) United States Patent
Klaassen et al.

(10) Patent No.: US 9,551,015 B2
(45) Date of Patent: *Jan. 24, 2017

(54) FERMENTATIVE PRODUCTION OF ETHANOL FROM GLUCOSE, GALACTOSE AND ARABINOSE EMPLOYING A RECOMBINANT YEAST STRAIN

(75) Inventors: Paul Klaassen, Dordrecht (NL); Gijsberdina Pieternella Van Suylekom, 'S Gravenmoer (NL); Bianca Elisabeth Maria Gielesen, Maasslius (NL); Nicolette Jasmijn Broers, Delft (NL); Beate Wiedemann, Leipzig (DE); Wilhelmus Theodorus Antonius Maria De Laat, Breda (NL)

(73) Assignee: DSM IP ASSETS B.V., Heerlen (NL)

( * ) Notice: Subject to any disclaimer, the term of this patent is extended or adjusted under 35 U.S.C. 154(b) by 479 days.

This patent is subject to a terminal disclaimer.

(21) Appl. No.: 13/383,190

(22) PCT Filed: Jul. 6, 2010

(86) PCT No.: PCT/EP2010/059618
§ 371 (c)(1),
(2), (4) Date: Jan. 20, 2012

(87) PCT Pub. No.: WO2011/003893
PCT Pub. Date: Jan. 13, 2011

(65) Prior Publication Data
US 2012/0115186 A1 May 10, 2012

(30) Foreign Application Priority Data
Jul. 10, 2009 (EP) .................... 09165229

(51) Int. Cl.
*C12P 1/02* (2006.01)
*C12P 7/10* (2006.01)

(52) U.S. Cl.
CPC *C12P 7/10* (2013.01); *Y02E 50/16* (2013.01); *Y02E 50/17* (2013.01); *Y02E 50/343* (2013.01)

(58) Field of Classification Search
CPC ........................................................ C12P 7/10
USPC ........................................................ 435/7.31
See application file for complete search history.

(56) References Cited

U.S. PATENT DOCUMENTS

2010/0086965 A1  4/2010  Van Maris et al.
2011/0104736 A1  5/2011  Pronk et al.

FOREIGN PATENT DOCUMENTS

WO    2008/041840     4/2008
WO    2009/011591     1/2009
WO    2009/109633     9/2009
WO    2010103530 A1   9/2010

OTHER PUBLICATIONS

Wisselink et al. "Engineering of *Saccharomyces cerevisiae* for efficient anaerobic alcoholic fermentation of L-arabinose", Applied and Environmental Microbiology, 2007, 73(15):4881-4891.*
Lee et al. "Biological conversion of lignocellulosic biomass to ethanol", J of Biotechnology, 1997, 56:1-24.*
Traff et al. "Deletion of the GRE3 aldose reductase gene and its influence on xylose metabolism in recombinant strains of *Saccharomyces cerevisiae* espressing the xylA and XKS1 genes", Applied and Environmental Microbiology, 2001, 67(12):5668-5674.*
Moniruzzaman et al. "Fermentation of corn fibre sugars by an engineered xylose utilizing *Saccharomyces* yeast strain", World J of Microbiology & Biotechnology, 1997, 13:341-346.*
Lekkas et al. "Elucidation of the role of nitrogenous wort components in yeast fermentation", J of Institute of Brewing & Distilling, 2007, 113:3-8.*
Wisselink et al., "Novel Evolutionary Engineering Approach for Accelerated Utilization of Glucose, Xylose, and Arabinose Mixtures by Engineered *Saccharomyces cerevisiae* Strains," Applied and Environmental Microbiology, vol. 75, No. 4, pp. 907-914 (Feb. 2009).
Van Maris et al., "Alcoholic Fermentation of Carbon Sourses in Biomass Hydrolysates by *Saccharomyces cerevisiae*: Current Status," Antonie van Leeuwenhoek, vol. 90, No. 4, pp. 391-418, (Nov. 2006).
International Search Report for PCT/EP2010/059618 Mailed Sep. 2, 2010.
Brink et al., "Energetic limits to metabolic flexibility: responses of *Saccharomyces cerevisiae* to glucose-galactose transitions," Microbiology (2009), 155, 1340-1350.
Australian Patent Oppositions—Acknowledge SGP, issued in Application No. 2010270301, DSM IP Assets B.V.; Opponent Novozymes A/S; Sep. 18, 2015.
Wisselink et al., "Engineering of *Saccharomyces cerevisiae* for Efficient Anaerobic Alcoholic Fermentation of L-Arabinose." Applied and Environmental Microbiology, 73(15) Aug. 2007, 4881-4891.
Van Den Brink et al., "Energetic limits to metabolic flexibility: responses of *Saccharomyces cerevisiae* to glucose-galactose transitions," Microbiology (2009), 155, 1340-1350.
Moniruzzaman et al., "Fermentation of corn fibre sugars by an engineered xylose utilizing *Saccharomyces* yeast strain." World Journal of Microbiology and Biotechnology (1997), 13 341-346.

(Continued)

*Primary Examiner* — Bin Shen
(74) *Attorney, Agent, or Firm* — McBee Moore Woodward & Vanik IP, LLC

(57) ABSTRACT

The present invention relates to a process for the production of one or more fermentation product from a sugar composition, comprising the following steps:
a) fermentation of the sugar composition in the presence of a yeast belonging to the genera *Saccharomyces, Kluyveromyces, Candida, Pichia, Schizosaccharomyces, Hansenula, Kloeckera, Schwanniomyces* or *Yarrowia*,: and
b) recovery of the fermentation product,
wherein the yeast comprises the genes araA, araB and araD and the sugar composition comprises glucose, galactose and arabinose.

12 Claims, 20 Drawing Sheets

(56) References Cited

OTHER PUBLICATIONS

Statement of Grounds and Particulars in the matter of Australian Patent Application No. 2010270301 in the name of DSM IP Assets B.V. and Opposition thereto by Novozymes North America, Inc. Sep. 18, 2015.
Letter to Commisioner dated Sep. 18, 2015, Australian Patent Application No. 2010270301 in the Name of DSM IP Assets B.V. and Opposition thereto by Novozymes A/S.
Austalian Patent Oppositions—Acknowledge SGP, issued in Application No. 2010270301, DSM IP Assets B.V.; Opponent Novozymes A/S; Sep. 22, 2015.
Declaration of Yong-su Jin in the matter of Australian Patent Application No. 2010270301 in the name of DSM IP Assets B.V. and Opposition thereto by Novozymes North America, Inc., executed Dec. 14, 2015.
Exhibit "YJ-1" Yong-su Jin: List of journal publications.
Exhibit "YJ-2" Yong-su Jin: List of scientific conferences attended since 2002.
Exhibit "YJ-3" Yong-su Jin: Practice Note CM 7.
Exhtbit "YJ-4" Yong-su Jin: Codon-Optimized Bacterial Genes Improve L-Arabinose Fermentation in Recombinant *Saccharomyces cerevisiae*. Applied and Environmental Microbiology, 74(07) Apr. 2008, 2043-2050.
Exhibit "YJ-5" Google search results with "Galactose arabinose cerevisiae fermentation".
Exhibit "YJ-6" PubMed Query, cerevisiae arabinose engineering ethanol.
Exhibit "YJ-7" Google search query: arabinose cerevisiae engineering ethanol patent.
Exhibit "YJ-8" Becker et al., "A Modified *Saccharomyces cerevisiae* Strain That Consumes L-Arabinose and Produces Ethanol." Applied and Environmental Microbiology, 69(07) Jul. 2003, 4144-4150.
Exhibit "YJ-9" WO2009011591A2.
Exhibit "YJ-10" WO2008041840A1.
Exhibit "YJ-11" Wisselink et al., "Engineering of *Saccharomyces cerevisiae* for Efficient Anaerobic Alcoholic Fermentation of L-Arabinose." Applied and Environmental Micobiology, 73(15) Aug. 2007, 4881-4891.
Exhibit "YJ-12" Moniruzzaman et al., "Fermentation of corn fibre sugars by an engineered xylose utilizing *Saccharomyces* yeast strain." World Journal of Microbiology and Biotechnology (1997), 13 341-346.
Exhibit "YJ-13" Van Den Brink et al., "Energetic limits to metabolic flexibility: responses of *Saccharomyces cerevisiae* to glucose-galactose transitions." Microbiology (2009), 155, 1340-1350.
Exhibit "YJ-14" Raamsdonk et al., "Co-consumption of sugars or ethanol and glucose on a *Saccharomyces cerevisiae* strain deleted in the HXK2 gene." Yeast (2001) 18: 1023-1033.
Exhibit "YJ-15" WO2011003893A1.
Exhibit "YJ-15" Lee et al., "Improved Galactose Fermentation of *Saccharomyces cerevisiae* Through Inverse Metabolic Engineering." Biotechnology and Engineering (2011) 108(03) 621-631.
Becker et al., "A Modified *Sachharomyces cerevisiae* Strain That Consumes L-Arabonose and Produces Ethanol." Applied and Environmental Microbiology (2003) 4144-4150.
Raamsdonk et al., "Co-consumption of sugars or ethanol and glucose in a *Saccharomyces cerevisiae* strain deleted in the HXK2 gene." Yeast (2001) 18: 1023-1033.

\* cited by examiner

Panel a

Panel b

Panel a

Panel b

Panel a

Panel b

SEQUENCE LISTING

```
<160> NUMBER OF SEQ ID NOS: 23

<210> SEQ ID NO 1
<211> LENGTH: 1317
<212> TYPE: DNA
<213> ORGANISM: Artificial sequence
<220> FEATURE:
<223> OTHER INFORMATION: Bacteroides uniformis

<400> SEQUENCE: 1
```

```
atggcaacaa agagtatttt tcccggaata ggaaagatta aattcgaagg taaagagagc      60
aagaacccga tggcattccg ttattacgat gccgataaag taatcatggg taagaaaatg     120
agcgaatggc tgaagttcgc catggcatgg tggcacactc tttgcgcaga aggtggtgac     180
caattcggtg gcgaacaaa gaaattcccc tggaacggtg aggctgacaa ggttcaggct     240
gccaagaaca aatggacgc cggctttgaa ttcatgcaga aatgggtat cgaatactac     300 tgcttccacg atgtagacct ctgcgaagaa gccgagacca ttgaagaata cgaagccaac     360
ttgaaggaaa tcgtagcgta tgccaagcag aaacaagcag aaaccggcat caaactgttg     420
tggggtactg ccaacgtatt cggccatgcc cgctacatga atggtgcagc caccaatccc     480
gatttcgatg ttgtggcacg tgccgccatc aaatcaaaa acgccatcga cgctactatc     540
gaactgggag gctcaaacta tgtattctgg ggcggtcgcg aaggctacat gtcattgctg     600
aatacagacc agaagcgtga aaagagcac ctcgcacaga tgttgaccat cgcccgcgac     660
tatgcacgtg cccgcggctt caaaggtacc ttcttgattg aaccgaaacc gatggaacct     720
acaaaacacc agtatgatgt agacaccgaa accgttatcg gcttcttgaa ggctcacaat     780
ctggacaaag atttcaaggt gaacatcgaa gtgaaccacg ctactttggc gggccacacc     840
ttcgagcacg aactcgcagt agccgtagac aacggtatgc tcggctccat cgacgccaac     900
cgtggtgact accagaacgg ctgggataca gaccagttcc ccattgacaa cttcgaactg     960
acccaggcaa tgatgcaaat catccgtaac ggaggctttg gcaatggcgg tacaaacttc    1020
gatgccaaga cccgtcgcaa ctccaccgac ctggaagaca ttttcattgc ccacatcgcc    1080
ggtatggacg tgatggcacg tgcactggaa agtgcagcca aactgcttga agagtctcct    1140
tacaagaaga tgctggccga ccgctatgct tccttcgaca gtggtaaagg caaggaattt    1200
gaagatggca aactgacgct ggaggatttg gtagcttacg caaaagccaa cggtgagccg    1260
aaacagacca gcggcaagca ggaattgtat gaggcaatcg tgaatatgta ctgctaa      1317
```

<210> SEQ ID NO 2
<211> LENGTH: 1318
<212> TYPE: DNA
<213> ORGANISM: Artificial sequence
<220> FEATURE:
<223> OTHER INFORMATION: Bacteroides uniformis codon optimized sequence
<220> FEATURE:
<221> NAME/KEY: CDS
<222> LOCATION: (1)..(1314)

<400> SEQUENCE: 2

```
atg gct acc aag gaa tac ttc cca ggt att ggt aag atc aaa ttc gaa       48
Met Ala Thr Lys Glu Tyr Phe Pro Gly Ile Gly Lys Ile Lys Phe Glu
1               5                   10                  15 ggt aag gaa tcc aag aac cca atg gcc ttc aga tac tac gat gct gac       96
Gly Lys Glu Ser Lys Asn Pro Met Ala Phe Arg Tyr Tyr Asp Ala Asp
            20                  25                  30 aag gtt atc atg ggt aag aag atg tct gaa tgg tta aag ttc gct atg      144
Lys Val Ile Met Gly Lys Lys Met Ser Glu Trp Leu Lys Phe Ala Met
        35                  40                  45 gct tgg tgg cat acc ttg tgt gct gaa ggt ggt gac caa ttc ggt ggt      192
Ala Trp Trp His Thr Leu Cys Ala Glu Gly Gly Asp Gln Phe Gly Gly
    50                  55                  60 ggt acc aag aaa ttc cca tgg aac ggt gaa gct gac aag gtc caa gct      240
Gly Thr Lys Lys Phe Pro Trp Asn Gly Glu Ala Asp Lys Val Gln Ala
65                  70                  75                  80 gct aag aac aag atg gac gct ggt ttc gaa ttt atg caa aag atg ggt      288
```

```
                                                                                  -continued Ala Lys Asn Lys Met Asp Ala Gly Phe Glu Phe Met Gln Lys Met Gly
                        85                  90                  95 att gaa tac tac tgt ttc cac gat gtt gac ttg tgt gaa gaa gct gaa              336
Ile Glu Tyr Tyr Cys Phe His Asp Val Asp Leu Cys Glu Glu Ala Glu
                100                 105                 110 acc atc gaa gaa tac gaa gct aac ttg aag gaa att gtt gct tac gct              384
Thr Ile Glu Glu Tyr Glu Ala Asn Leu Lys Glu Ile Val Ala Tyr Ala
            115                 120                 125 aag caa aag caa gct gaa act ggt atc aag cta tta tgg ggt act gct              432
Lys Gln Lys Gln Ala Glu Thr Gly Ile Lys Leu Leu Trp Gly Thr Ala
        130                 135                 140 aac gtc ttt ggt cat gcc aga tac atg aac ggt gcc gct acc aac cca              480
Asn Val Phe Gly His Ala Arg Tyr Met Asn Gly Ala Ala Thr Asn Pro
145                 150                 155                 160 gat ttc gat gtt gtt gcc aga gct gcc atc caa atc aag aac gcc atc              528
Asp Phe Asp Val Val Ala Arg Ala Ala Ile Gln Ile Lys Asn Ala Ile
                165                 170                 175 gat gct acc att gaa tta ggt ggt tcc aac tac gtt ttc tgg ggt ggt              576
Asp Ala Thr Ile Glu Leu Gly Gly Ser Asn Tyr Val Phe Trp Gly Gly
            180                 185                 190 aga gaa ggt tac atg tcc ttg ttg aac act gac caa aag aga gaa aag              624
Arg Glu Gly Tyr Met Ser Leu Leu Asn Thr Asp Gln Lys Arg Glu Lys
        195                 200                 205 gaa cac ttg gct caa atg ttg acc att gct cgt gac tac gct cgt gcc              672
Glu His Leu Ala Gln Met Leu Thr Ile Ala Arg Asp Tyr Ala Arg Ala
210                 215                 220 aga ggt ttc aag ggt act ttc ttg att gaa cca aag cca atg gaa cca              720
Arg Gly Phe Lys Gly Thr Phe Leu Ile Glu Pro Lys Pro Met Glu Pro
225                 230                 235                 240 acc aag cac caa tac gat gtt gac acc gaa act gtc atc ggt ttc ttg              768
Thr Lys His Gln Tyr Asp Val Asp Thr Glu Thr Val Ile Gly Phe Leu
                245                 250                 255 aag gct cac aac ttg gac aag gac ttc aag gtc aac atc gaa gtc aac              816
Lys Ala His Asn Leu Asp Lys Asp Phe Lys Val Asn Ile Glu Val Asn
            260                 265                 270 cac gct act ttg gcc ggt cac act ttc gaa cac gaa ttg gct gtt gct              864
His Ala Thr Leu Ala Gly His Thr Phe Glu His Glu Leu Ala Val Ala
        275                 280                 285 gtc gac aac ggt atg ttg ggt tcc att gat gct aac aga ggt gac tac              912
Val Asp Asn Gly Met Leu Gly Ser Ile Asp Ala Asn Arg Gly Asp Tyr
290                 295                 300 caa aac ggt tgg gac acc gac caa ttc cca atc gac aac ttt gaa ttg              960
Gln Asn Gly Trp Asp Thr Asp Gln Phe Pro Ile Asp Asn Phe Glu Leu
305                 310                 315                 320 act caa gct atg atg caa atc atc aga aac ggt ggt ttc ggt aac ggt             1008
Thr Gln Ala Met Met Gln Ile Ile Arg Asn Gly Gly Phe Gly Asn Gly
                325                 330                 335 ggt acc aac ttc gat gct aag acc aga aga aac tct act gac ttg gaa             1056
Gly Thr Asn Phe Asp Ala Lys Thr Arg Arg Asn Ser Thr Asp Leu Glu
            340                 345                 350 gat atc ttc atc gct cac att gcc ggt atg gat gtc atg gcc aga gct             1104
Asp Ile Phe Ile Ala His Ile Ala Gly Met Asp Val Met Ala Arg Ala
        355                 360                 365 ttg gaa tct gct gct aaa tta ttg gaa gaa tct cct tac aag aag atg             1152
Leu Glu Ser Ala Ala Lys Leu Leu Glu Glu Ser Pro Tyr Lys Lys Met
370                 375                 380 ttg gct gac aga tac gct tct ttc gac tct ggt aag ggt aag gaa ttt             1200
Leu Ala Asp Arg Tyr Ala Ser Phe Asp Ser Gly Lys Gly Lys Glu Phe
385                 390                 395                 400
```

-continued

```
gaa gat ggt aag ttg act ttg gaa gat ttg gtt gct tac gcc aag gct      1248
Glu Asp Gly Lys Leu Thr Leu Glu Asp Leu Val Ala Tyr Ala Lys Ala
            405                 410                 415 aac ggt gaa cca aag caa act tct ggt aag caa gaa ttg tac gaa gcc      1296
Asn Gly Glu Pro Lys Gln Thr Ser Gly Lys Gln Glu Leu Tyr Glu Ala
        420                 425                 430 att gtc aac atg tac tgt taag                                         1318
Ile Val Asn Met Tyr Cys
        435
```

<210> SEQ ID NO 3
<211> LENGTH: 438
<212> TYPE: PRT
<213> ORGANISM: Artificial sequence
<220> FEATURE:
<223> OTHER INFORMATION: Synthetic Construct

<400> SEQUENCE: 3

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asp
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Lys Phe Pro Trp Asn Gly Glu Ala Asp Lys Val Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Ile Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300
```

| | | | | | | | | | | | |
|---|---|---|---|---|---|---|---|---|---|---|---|
|Gln|Asn|Gly|Trp|Asp|Thr|Asp|Gln|Phe|Pro|Ile|Asp|Asn|Phe|Glu|Leu|
|305| | | |310| | | |315| | | |320|

Thr Gln Ala Met Met Gln Ile Ile Arg Asn Gly Gly Phe Gly Asn Gly
            325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
            355                 360                 365

Leu Glu Ser Ala Ala Lys Leu Leu Glu Glu Ser Pro Tyr Lys Lys Met
370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Val Ala Tyr Ala Lys Ala
            405                 410                 415

Asn Gly Glu Pro Lys Gln Thr Ser Gly Lys Gln Glu Leu Tyr Glu Ala
            420                 425                 430

Ile Val Asn Met Tyr Cys
            435

<210> SEQ ID NO 4
<211> LENGTH: 16176
<212> TYPE: DNA
<213> ORGANISM: Artificial sequence
<220> FEATURE:
<223> OTHER INFORMATION: Synthetic DNA

<400> SEQUENCE: 4

```
tcgcgcgttt cggtgatgac ggtgaaaacc tcttgacaca tgcagctccc ggagacggtc      60
acagcttgtc tgtaagcgga tgccgggagc agacaagccc gtcagggcgc gtcagcgggt     120
gttggcgggt gtcggggctg gcttaactat gcggcatcag agcagattgt actgagagtg     180
caccatatgc ggtgtgaaat accgcacaga tgcgtaagga gaaaataccg catcaggcgc     240
cattcgccat tcaggctgcg caactgttgg gaagggcgat cggtgcgggc ctcttcgcta     300
ttacgccagc tggcgaaagg gggatgtgct gcaaggcgat taagttgggt aacgccaggg     360
ttttcccagt cacgacgttg taaaacgacg gccagtaagc ttgcatgcct gcaggtcgac     420
gcggccgcat atttttttgta actgtaattt cactcatgca caagaaaaaa aaaactggat     480
taaaagggag cccaaggaaa actcctcagc atatatttag aagtctcctc agcatatagt     540
tgtttgtttt ctttacacat tcactgttta ataaaacttt tataatattt cattatcgga     600
actctagatt ctatacttgt ttcccaattg ggccgatcgg ccttgctgg tagtaaacgt      660 atacgtcata aaagggaaaa gccacatgcg gaagaatttt atggaaaaaa aaaaaccctc     720
gaagttacta cttctagggg gcctatcaag taaattactc ctggtacact gaagtatata     780
agggatatag aagcaaatag ttgtcagtgc aatccttcaa gacgattggg aaaatactgt     840
aggtaccgga gacctaacta catagtgttt aaagattacg gatatttaac ttacttagaa     900
taatgccatt tttttgagtt ataataatcc tacgttagtg tgagcgggat ttaaactgtg     960
aggaccttaa tacattcaga cacttctgcg gtatcaccct acttattccc ttcgagatta    1020
tatctaggaa cccatcaggt tggtggaaga ttacccgttc taagactttt cagcttcctc    1080
tattgatgtt acacctggac accccttttc tggcatccag ttttttaatct tcagtggcat    1140 gtgagattct ccgaaattaa ttaaagcaat cacacaattc tctcggatac cacctcggtt    1200
gaaactgaca ggtggtttgt tacgcatgct aatgcaaagg agcctatata cctttggctc    1260
```

```
ggctgctgta acagggaata taaagggcag cataatttag gagtttagtg aacttgcaac     1320
atttactatt ttcccttctt acgtaaatat ttttcttttt aattctaaat caatctttt     1380 caattttttg tttgtattct tttcttgctt aaatctataa ctacaaaaaa cacatacata     1440
aactaaaaat gtctgaacca gctcaaaaga aacaaaaggt tgctaacaac tctctagaac     1500
aattgaaagc ctccggcact gtcgttgttg ccgacactgg tgatttcggc tctattgcca     1560
agtttcaacc tcaagactcc acaactaacc catcattgat cttggctgct gccaagcaac     1620
caacttacgc caagttgatc gatgttgccg tggaatacgg taagaagcat ggtaagacca     1680
ccgaagaaca agtcgaaaat gctgtggaca gattgttagt cgaattcggt aaggagatct     1740
taaagattgt tccaggcaga gtctccaccg aagttgatgc tagattgtct tttgacactc     1800
aagctaccat tgaaaaggct agacatatca ttaaattgtt tgaacaagaa ggtgtctcca     1860
aggaaagagt ccttattaaa attgcttcca cttgggaagg tattcaagct gccaaagaat     1920
tggaagaaaa ggacggtatc cactgtaatt tgactctatt attctccttc gttcaagcag     1980
ttgcctgtgc cgaggcccaa gttactttga tttccccatt tgttggtaga attctagact     2040
ggtacaaatc cagcactggt aaagattaca agggtgaagc cgacccaggt gttatttccg     2100
tcaagaaaat ctacaactac tacaagaagt acggttacaa gactattgtt atgggtgctt     2160 cttttcagaag cactgacgaa atcaaaaact tggctggtgt tgactatcta acaatttctc     2220
cagctttatt ggacaagttg atgaacagta ctgaaccttt cccaagagtt ttggaccctg     2280
tctccgctaa gaaggaagcc ggcgacaaga tttcttacat cagcgacgaa tctaaattca     2340
gattcgactt gaatgaagac gctatggcca ctgaaaaatt gtccgaaggt atcagaaaat     2400
tctctgccga tattgttact ctattcgact tgattgaaaa gaaagttacc gcttaaggaa     2460
gtatctcgga aatattaatt taggccatgt ccttatgcac gtttcttttg atacttacgg     2520
gtacatgtac acaagtatat ctatatatat aaattaatga aaatcccctta tttatatata     2580 tgactttaac gagacagaac agttttttat ttttttatcct atttgatgaa tgatacagtt     2640
tcttattcac gtgttatacc cacaccaaat ccaatagcaa taccggccat cacaatcact     2700
gtttcggcag cccctaagat cagacaaaac atccggaacc accttaaatc aacgtcccat     2760
atgaatcctt gcagcaaagc cgctcgtacc ggagatatac aatagaacag ataccagaca     2820
agacataatg ggctaaacaa gactacacca attacactgc ctcattgatg gtggtacata     2880
acgaactaat actgtagccc tagacttgat agccatcatc atatcgaagt tcactaccc      2940 tttttccatt tgccatctat tgaagtaata ataggcgcat gcaacttctt ttcttttttt     3000 ttctttttctc tctcccccgt tgttgtctca ccatatccgc aatgacaaaa aaatgatgga     3060
agacactaaa ggaaaaaatt aacgacaaag acagcaccaa cagatgtcgt tgttccagag     3120
ctgatgaggg gtatctcgaa gcacacgaaa cttttttcctt ccttcattca cgcacactac     3180
tctctaatga gcaacggtat acggccttcc ttccagttac ttgaatttga aataaaaaaa     3240
agtttgctgt cttgctatca agtataaata gacctgcaat tattaatctt ttgtttcctc     3300
gtcattgttc tcgttcccctt tcttccttgt ttctttttct gcacaatatt tcaagctata     3360
ccaagcatac aatcaactat ctcatataca atgactcaat tcactgacat tgataagcta     3420
gccgtctcca ccataagaat tttggctgtg acaccgtat ccaaggccaa ctcaggtcac      3480
ccaggtgctc cattgggtat ggcaccagct gcacacgttc tatggagtca aatgcgcatg     3540
aacccaacca acccagactg gatcaacaga gatagatttg tcttgtctaa cggtcacgcg     3600
gtcgctttgt tgtattctat gctacatttg actggttacg atctgtctat tgaagacttg     3660
```

```
aaacagttca gacagttggg ttccagaaca ccaggtcatc ctgaatttga gttgccaggt    3720
gttgaagtta ctaccggtcc attaggtcaa ggtatctcca acgctgttgg tatggccatg    3780
gctcaagcta acctggctgc cacttacaac aagccgggct ttaccttgtc tgacaactac    3840
acctatgttt tcttgggtga cggttgtttg caagaaggta tttcttcaga gcttcctcc     3900 ttggctggtc atttgaaatt gggtaacttg attgccatct acgatgacaa caagatcact    3960
atcgatggtg ctaccagtat ctcattcgat gaagatgttg ctaagagata cgaagcctac    4020
ggttgggaag ttttgtacgt agaaaatggt aacgaagatc tagccggtat tgccaaggct    4080
attgctcaag ctaagttatc caaggacaaa ccaactttga tcaaaatgac cacaaccatt    4140
ggttacggtt ccttgcatgc cggctctcac tctgtgcacg gtgccccatt gaaagcagat    4200
gatgttaaac aactaaagag caaattcggt ttcaacccag acaagtcctt tgttgttcca    4260
caagaagttt acgaccacta ccaaaagaca attttaaagc caggtgtcga agccaacaac    4320
aagtggaaca agttgttcag cgaataccaa aagaaattcc cagaattagg tgctgaattg    4380
gctagaagat tgagcggcca actacccgca aattgggaat ctaagttgcc aacttacacc    4440
gccaaggact ctgccgtggc cactagaaaa ttatcagaaa ctgttcttga ggatgtttac    4500
aatcaattgc cagagttgat tggtggttct gccgatttaa caccttctaa cttgaccaga    4560
tggaaggaag cccttgactt ccaacctcct tcttccggtt caggtaacta ctctggtaga    4620
tacattaggt acggtattag agaacacgct atgggtgcca taatgaacgg tatttcagct    4680
ttcggtgcca actacaaacc atacggtggt actttcttga acttcgtttc ttatgctgct    4740
ggtgccgtta gattgtccgc tttgtctggc cacccagtta tttgggttgc tacacatgac    4800
tctatcggtg tcggtgaaga tggtccaaca catcaaccta ttgaaacttt agcacacttc    4860
agatccctac caaacattca agtttggaga ccagctgatg taacgaagt ttctgccgcc     4920 tacaagaact ctttagaatc caagcatact ccaagtatca ttgctttgtc cagacaaaac    4980
ttgccacaat tggaaggtag ctctattgaa agcgcttcta agggtggtta cgtactacaa    5040
gatgttgcta acccagatat tattttagtg ctactggtt ccgaagtgtc tttgagtgtt     5100
gaagctgcta agactttggc cgcaaagaac atcaaggctc gtgttgtttc tctaccagat    5160
ttcttcactt tgacaaaca accctagaa tacagactat cagtcttacc agacaacgtt      5220
ccaatcatgt ctgttgaagt tttggctacc acatgtgggg gcaaatacgc tcatcaatcc    5280
ttcggtattg acagatttgg tgcctccggt aaggcaccag aagtcttcaa gttcttcggt    5340
ttcaccccag aaggtgttgc tgaaagagct caaaagacca ttgcattcta aagggtgac    5400 aagctaattt ctcctttgaa aaaagctttc taaattctga tcgtagatca tcagatttga    5460
tatgatatta tttgtgaaaa aatgaaataa aactttatac aacttaaata caactttttt    5520
tataaacgat taagcaaaaa aatagtttca aacttttaac aatattccaa acactcagtc    5580
cttttccttc ttatattata ggtgtacgta ttatagaaaa atttcaatga ttactttttc    5640 tttcttttc cttgtaccag cacatggccg agcttgaatg ttaaacccttt cgagagaatc     5700 acaccattca agtataaagc caataaagaa tatcgtacca gagaatttg ccatcggaca     5760 tgctacctta cgcttatatc tctcattgga atatcgtttt ctgattaaaa cacggaagta    5820
agaacttaat tcgttttccg ttgaactatg ttgtgccagc gtaacattaa aaaagagtgt    5880
acaaggccac gttctgtcac cgtcagaaaa atatgtcaat gaggcaagaa ccggatggt     5940 aacaaaaatc acgatctggg tgggtgtggg tgtattggat tataggaagc cacgcgctca    6000
```

```
acctggaatt acaggaagct ggtaattttt tgggtttgca atcatcacca tctgcacgtt    6060
gttataatgt cccgtgtcta tatatatcca ttgacggtat tctatttttt tgctattgaa    6120
atgagcgttt tttgttacta caattggttt tacagacgga attttcccta tttgtttcgt    6180 cccattttc cttttctcat tgttctcata tcttaaaaag gtcctttctt cataatcaat     6240
gctttctttt acttaatatt ttacttgcat tcagtgaatt ttaatacata ttcctctagt    6300
cttgcaaaat cgatttagaa tcaagatacc agcctaaaaa tggtcaaacc aattatagct    6360
cccagtatcc ttgcttctga cttcgccaac ttgggttgcg aatgtcataa ggtcatcaac    6420
gccggcgcag attggttaca tatcgatgtc atggacggcc attttgttcc aaacattact    6480
ctgggccaac caattgttac ctccctacgt cgttctgtgc cacgccctgg cgatgctagc    6540
aacacagaaa agaagcccac tgcgttcttc gattgtcaca tgatggttga aaatcctgaa    6600
aaatgggtcg acgattttgc taaatgtggt gctgaccaat ttacgttcca ctacgaggcc    6660
acacaagacc ctttgcattt agttaagttg attaagtcta agggcatcaa agctgcatgc    6720
gccatcaaac ctggtacttc tgttgacgtt ttatttgaac tagctcctca tttgatatg    6780 gctcttgtta tgactgtgga acctgggttt ggaggccaaa aattcatgga agacatgatg    6840
ccaaaagtgg aaactttgag agccaagttc ccccatttga atatccaagt cgatggtggt    6900
ttgggcaagg agaccatccc gaaagccgcc aaagccggtg ccaacgttat tgtcgctgga    6960
accagtgttt tcactgcagc tgacccgcac gatgttatct ccttcatgaa agaagaagtc    7020
tcgaaggaat tgcgttctag agatttgcta gattagttgt acatatgcgg catttcttat    7080
atttatactc tctatactat acgatatggt attttttct cgttttgatc tcctaatata    7140
cataaaccga gccattccta ctatacaaga tacgtaagtg cctaactcat gggaaaaatg    7200
ggccgcccag ggtggtgcct tgtccgtttt cgatgatcaa tccctgggat gcagtatcgt    7260
caatgacact ccataaggct tccttaacca aagtcaaaga actcttcttt tcattctctt    7320
tcactttctt accgccatct agatcaatat ccatttcgta ccccgcggaa ccgccagata    7380
ttcattactt gacgcaaaag cgtttgaaat aatgacgaaa agaaggaag aaaaaaaaag    7440 aaaaataccg cttctaggcg ggttatctac tgatccgagc ttccactagg atagcaccca    7500
aacacctgca tatttggacg accttacttt acaccaccaa aaaccacttt cgcctctccc    7560
gcccctgata acgtccacta attgagcgat tacctgagcg gtcctctttt gtttgcagca    7620
tgagacttgc atactgcaaa tcgtaagtag caacgtctca aggtcaaaac tgtatggaaa    7680
ccttgtcacc tcacttaatt ctagctagcc taccctgcaa gtcaagaggt ctccgtgatt    7740
cctagccacc tcaaggtatg cctctccccg gaaactgtgg cctttctgg cacacatgat    7800 ctccacgatt tcaacatata aatagctttt gataatggca atattaatca aatttatttt    7860
acttctttct tgtaacatct ctcttgtaat cccttattcc ttctagctat ttttcataaa    7920
aaaccaagca actgcttatc aacacacaaa cactaaatca aaatggctgc cggtgtccca    7980
aaaattgatg cgttagaatc tttgggcaat ccttttggagg atgccaagag agctgcagca    8040
tacagagcag ttgatgaaaa tttaaaattt gatgatcaca aaattattgg aattggtagt    8100
ggtagcacag tggtttatgt tgccgaaaga attggacaat atttgcatga ccctaaattt    8160
tatgaagtag cgtctaaatt catttgcatt ccaacaggat tccaatcaag aaacttgatt    8220
ttggataaca agttgcaatt aggctccatt gaacagtatc ctcgcattga tatagcgttt    8280
gacggtgctg atgaagtgga tgagaattta caattaatta aaggtggtgg tgcttgtcta    8340
tttcaagaaa aattggttag tactagtgct aaaaccttca ttgtcgttgc tgattcaaga    8400
```

```
aaaaagtcac caaaacattt aggtaagaac tggaggcaag gtgttcccat tgaaattgta    8460
ccttcctcat acgtgagggt caagaatgat ctattagaac aattgcatgc tgaaaaagtt    8520
gacatcagac aaggaggttc tgctaaagca ggtcctgttg taactgacaa taataacttc    8580
attatcgatg cggatttcgg tgaaatttcc gatccaagaa aattgcatag agaaatcaaa    8640
ctgttagtgg gcgtggtgga aacaggttta ttcatcgaca acgcttcaaa agcctacttc    8700
ggtaattctg acggtagtgt tgaagttacc gaaaagtgag cagatcaaag caaagacag    8760 aaaccgtagt aaaggttgac ttttcacaac agtgtctcca tttttatat tgtattatta    8820 aagctattta gttatttgga tactgttttt tttccagaag ttttctttt agtaaagtac    8880 aatccagtaa aaatgaagga tgaacaatcg gtgtatgcag attcaacacc aataaatgca    8940
atgtttattt ctttggaacg tttgtgttgt tcgaaatcca ggataatcct tcaacaagac    9000
cctgtccgga taaggcgtta ctaccgatga cacaccaagc tcgagtaacg gagcaagaat    9060
tgaaggatat ttctgcacta aatgccaaca tcagatttaa tgatccatgg acctggttgg    9120
atggtaaatt ccccactttt gcctgatcca gccagtaaaa tccatactca acgacgatat    9180
gaacaaattt ccctcattcc gatgctgtat atgtgtataa attttacat gctcttctgt    9240 ttagacacag aacagcttta aataaaatgt tggatatact ttttctgcct gtggtgtcat    9300
ccacgctttt aattcatctc ttgtatggtt gacaatttgg ctatttttta acagaaccca    9360
acggtaattg aaattaaaag ggaaacgagt gggggcgatg agtgagtgat actaaaatag    9420
acaccaagag agcaaagcgg tcccagcggc cgcgaattcg gcgtaatcat ggtcatagct    9480
gtttcctgtg tgaaattgtt atccgctcac aattccacac aacatacgag ccggaagcat    9540
aaagtgtaaa gcctggggtg cctaatgagt gagctaactc acattaattg cgttgcgctc    9600
actgcccgct ttccagtcgg gaaacctgtc gtgccagctg cattaatgaa tcggccaacg    9660
cgcggggaga ggcggtttgc gtattgggcg ctcttccgct tcctcgctca ctgactcgct    9720
gcgctcggtc gttcggctgc ggcgagcggt atcagctcac tcaaaggcgg taatacggtt    9780
atccacagaa tcaggggata acgcaggaaa gaacatgtga gcaaaaggcc agcaaaaggc    9840
caggaaccgt aaaaaggccg cgttgctggc gttttccat aggctccgcc ccctgacga    9900 gcatcacaaa aatcgacgct caagtcagag gtggcgaaac ccgacaggac tataaagata    9960
ccaggcgttt ccccctggaa gctccctcgt gcgctctcct gttccgaccc tgccgcttac   10020
cggatacctg tccgcctttc tcccttcggg aagcgtggcg ctttctcaat gctcacgctg   10080
taggtatctc agttcggtgt aggtcgttcg ctccaagctg ggctgtgtgc acgaaccccc   10140
cgttcagccc gaccgctgcg ccttatccgg taactatcgt cttgagtcca acccggtaag   10200
acacgactta tcgccactgg cagcagccac tggtaacagg attagcagag cgaggtatgt   10260
aggcggtgct acagagttct tgaagtggtg gcctaactac ggctacacta aggacagt   10320 atttggtatc tgcgctctgc tgaagccagt taccttcgga aaagagttg gtagctcttg   10380 atccggcaaa caaaccaccg ctggtagcgg tggtttttt gtttgcaagc agcagattac   10440
gcgcagaaaa aaaggatctc aagaagatcc tttgatcttt tctacggggt ctgacgctca   10500
gtggaacgaa aactcacgtt aagggatttt ggtcatgaga ttatcaaaaa ggatcttcac   10560
ctagatcctt ttaaattaaa aatgaagttt taaatcaatc taagtatat atgagtaaac   10620 ttggtctgac agttaccaat gcttaatcag tgaggcacct atctcagcga tctgtctatt   10680
tcgttcatcc atagttgcct gactccccgt cgtgtagata actacgatac gggagggctt   10740
```

```
accatctggc cccagtgctg caatgatacc gcgagaccca cgctcaccgg ctccagattt   10800
atcagcaata aaccagccag ccggaagggc cgagcgcaga agtggtcctg caactttatc   10860
cgcctccatc cagtctatta attgttgccg ggaagctaga gtaagtagtt cgccagttaa   10920
tagtttgcgc aacgttgttg ccattgctac aggcatcgtg gtgtcacgct cgtcgtttgg   10980
tatggcttca ttcagctccg gttcccaacg atcaaggcga gttacatgat cccccatgtt   11040
gtgcaaaaaa gcggttagct ccttcggtcc tccgatcgtt gtcagaagta agttggccgc   11100
agtgttatca ctcatggtta tggcagcact gcataattct cttactgtca tgccatccgt   11160
aagatgcttt tctgtgactg gtgagtactc aaccaagtca ttctgagaat agtgtatgcg   11220
gcgaccgagt tgctcttgcc cggcgtcaat acgggataat accgcgccac atagcagaac   11280
tttaaaagtg ctcatcattg gaaaacgttc ttcggggcga aaactctcaa ggatcttacc   11340
gctgttgaga tccagttcga tgtaacccac tcgtgcaccc aactgatctt cagcatcttt   11400
tactttcacc agcgtttctg ggtgagcaaa aacaggaagg caaaatgccg caaaaaaggg   11460
aataagggcg acacggaaat gttgaatact catactcttc cttttcaat attattgaag   11520 catttatcag ggttattgtc tcatgagcgg atacatattt gaatgtattt agaaaaataa   11580
acaaataggg gttccgcgca catttccccg aaaagtgcca cctgacgtca actatacaaa   11640
tgacaagttc ttgaaaacaa gaatcttttt attgtcagta ctgattagaa aaactcatcg   11700
agcatcaaat gaaactgcaa tttattcata tcaggattat caataccata ttttgaaaa   11760 agccgtttct gtaatgaagg agaaaactca ccgaggcagt tccataggat ggcaagatcc   11820
tggtatcggt ctgcgattcc gactcgtcca acatcaatac aacctattaa tttcccctcg   11880
tcaaaaataa ggttatcaag tgagaaatca ccatgagtga cgactgaatc cggtgagaat   11940
ggcaaaagct tatgcatttc tttccagact tgttcaacag gccagccatt acgctcgtca   12000
tcaaaatcac tcgcatcaac caaaccgtta ttcattcgtg attgcgcctg agcgagacga   12060
aatacgcgat cgctgttaaa aggacaatta caaacaggaa tcgaatgcaa ccggcgcagg   12120
aacactgcca gcgcatcaac aatattttca cctgaatcag gatattcttc taatacctgg   12180
aatgctgttt tgccggggat cgcagtggtg agtaaccatg catcatcagg agtacggata   12240
aaatgcttga tggtcggaag aggcataaat tccgtcagcc agtttagtct gaccatctca   12300
tctgtaacat cattggcaac gctacctttg ccatgtttca gaaacaactc tggcgcatcg   12360
ggcttcccat acaatcgata gattgtcgca cctgattgcc cgacattatc gcgagcccat   12420
ttatacccat ataaatcagc atccatgttg gaatttaatc gcggcctcga acgtgagtc   12480 ttttccttac ccatggttgt ttatgttcgg atgtgatgtg agaactgtat cctagcaaga   12540
ttttaaaagg aagtatatga agaagaacc tcagtggcaa atcctaacct tttatatttc   12600
tctacagggg cgcggcgtgg ggacaattca acgcgactgt gacgcgttct agaacacaca   12660
atatgcatgt aatcgctgat ttttttttgtt ttagaagctc tatcttcagg taaaaatgag   12720
tagagaaaaa aaacatact ggatcgatgc agaattaggg ggttattatc ctgcaggtac   12780
atgattttca gtgggaacat tgctttttag tagtccggtt ctcaacaact tgtctaagtg   12840
ttgaaaacaa aagaaatggc gtagaaacaa agtagtgtaa gtaaatctgc caatgttcta   12900
tgtataaaaa gtaaaggcaa gaagaggttc tatgcatatt tctgaaaata tctaatacac   12960
tattataatg catcaagaaa ctgtcgtatg atgaagtgcc tatgagtttt tgtgtacgtg   13020
cttctctagt atgtagccgg ttttctcttt ttacctcttt ttactactta tactactact   13080
tttactacct ttcttccacg taatctagat ctcaagccac aattcttgcc ctatgctcca   13140
```

```
acgtatacaa catcgaagaa gagtctttct ttagggagtc attggaaaag atagtatgat   13200
ggtattcgat ttacctatgt cgcaaaagaa agtccggggc aacaccacag aatgctttct   13260
ctgtactaat aacctgttgt gcgcttaacg gtctaatcgt taatcagcgg tggttaaatt   13320
tttgtaaatc taatgttcca tgattttctt tcttcaaaag gaacatgtag cgaaaatctt   13380 tttttttactt tgatacactg caattgtttc tgagcatgct gaaattttct cgatgttttt   13440
tttttttatt ggcatccaag taattaatcc ttatgctacg aaaagttgt aggaatgaat    13500 catgcataat ctaacggata tcatcatata ctctgtgcta atattctaaa caagttcgaa   13560
aatattttct tggcccatgt aataggtggt aagtgtattg ctttgatagg aacgtcatta   13620
tcgcacaaga caatcggcac taataaccgt ttaaatatta tcatgcatgt atacatcagt   13680
atctcataga aatatacctg taagtacata cttatctaag tataaattct cgacctatgg   13740
agtcaccaca tttcccagca acttccccac ttcctctgca atcgccaacg tcctctcttc   13800
actgagtctc cgtccgataa cctgcactgc aaccggtgcc ccatggtacg cctccggatc   13860
atactcttcc tgcacgaggg catcaagctc actaaccgcc ttgaaactct cattcttctt   13920
atcgatgttc ttatccgcaa aggtaaccgg aacaaccacg ctcgtgaaat ccagcaggtt   13980
gatcacagag gcatacccat agtaccggaa ctggtcatgc cgtaccgcag cggtaggcgt   14040
aatcggcgcg atgatggcgt ccagttcctt cccggccttt tcttcagcct cccgccattt   14100
ctcaaggtac tccatctggt aattccactt ctggagatgc gtgtcccaga gctcgttcat   14160
gttaacagct ttgatgttcg ggttcagtag gtctttgata tttggaatcg ccggctcgcc   14220
ggatgcactg atatcgcgca ttacgtcggc gctgccgtca gccgcgtaga tatgggagat   14280
gagatcgtgg ccgaaatcgt gcttgtatgg cgtccacggg gtcacggtgt gaccggcttt   14340
ggcgagtgcg gcgacggtgg tttccacgcc gcgcaggata ggagggtgtg gaaggacatt   14400
gccgtcgaag ttgtagtagc cgatattgag cccgccgttc ttgatcttgg aggcaataat   14460
gtccgactcg gactggcgcc agggcatggg gatgaccttg gagtcgtatt tccatggctc   14520
ctgaccgagg acggatttgg tgaagaggcg gaggtcctca acagagtgcg taatcggccc   14580
gacaacgctg tgcaccgtct cctgaccctc catgctgttc gccatctttg catacggcag   14640
ccgcccatga ctcggcctta gaccgtacag gaagttgaac gcggccggca ctcgaatcga   14700
gccaccgata tccgttccta caccgatgac gccaccacga atcccaacga tcgcaccctc   14760
accaccagaa ctgccgccgc acgaccagtt cttgttgcgt gggttgacgg tgcgcccgat   14820
gatgttgttg actgtctcgc agaccatcag ggtctgcggg acagaggtct tgacgtagaa   14880
gacggcaccg gctttgcgga gcatggttgt cagaaccgag tccccttcgt cgtacttgtt   14940
tagccatgag atgtagccca ttgatgtttc gtagcccttg actcgaagct ggtctttgag   15000
agagatgggg aggccatgga gtggaccaac gggtctcttg tgctttgcgt agtattcatc   15060
gagttccctt gcctgcgcga gagcggcgtc agggaagaac tcgtgggcgc agtttgttaa   15120
ctgctgggcg attgctgccc gtttacagaa tgctagcgta acttccaccg aggtcaactc   15180
tccggccgcc agcttggaca caagatctgc agcggaggcc tctgtgatct tcagttcggc   15240
ctctgaaagg atccccgatt tctttgggaa atcaataacg ctgtcttccg caggcagcgt   15300
ctggactttc cattcatcag ggatggtttt tgcgaggcgg gcgcgcttat cagcggccag   15360
ttcttcccag gattgaggca ttgtatatga gatagttgat tgtatgcttg gtatagcttg   15420
aaatattgtg cagaaaaaga aacaaggaag aaagggaacg agaacaatga cgaggaaaca   15480
```

-continued

```
aaagattaat aaattgcaggt ctatttatac ttgatagcaa agcggcaaac ttttttttatt    15540 tcaaattcaa gtaactggaa ggaaggccgt ataccgttgc tcattagaga gtagtgtgcg    15600
tgaatgaagg aaggaaaaag tttcgtgtgt tcgaagatac ccctcatcag ctctggaaca    15660 acgcacatctg ttggtgctgt cttttgtcgtt aattttttcc tttagtgtct tccatcattt    15720
tttttgtcat tgcggatatg gtgagacaac aacgggggag agagaaaaga aaaaaaaga    15780 aaagaagttg catgcgccta ttattacttc aatagatggc aaatgaaaaa agggtagtga    15840
aacttcgata tgatgatggc tatcaagtct agggctacag tattagttcg ttatgtacca    15900
ccatcaatga ggcagtgtaa tttgtgtagt cttgtttagc ccattatgtc ttgtctggta    15960
tctgttctat tgtatatctc ccctccgcca cctacatgtt agggagacca acgaaggtat    16020
tataggaatc ccgatgtatg ggtttggttg ccagaaaaga ggaagtccat attgtacacc    16080
cggaaacaac aaaaggatgg gcccatgacg tctaagaaac cattattatc atgacattaa    16140
cctataaaaa taggcgtatc acgaggccct ttcgtc                                16176
```

<210> SEQ ID NO 5
<211> LENGTH: 22
<212> TYPE: DNA
<213> ORGANISM: Artificial sequence
<220> FEATURE:
<223> OTHER INFORMATION: Synthetic DNA

<400> SEQUENCE: 5
gaaatgggcg cattactaca ag                                              22

<210> SEQ ID NO 6
<211> LENGTH: 22
<212> TYPE: DNA
<213> ORGANISM: Artificial sequence
<220> FEATURE:
<223> OTHER INFORMATION: Synthetic DNA

<400> SEQUENCE: 6
caccaacctg atgggttcct ag                                              22

<210> SEQ ID NO 7
<211> LENGTH: 22
<212> TYPE: DNA
<213> ORGANISM: Artificial sequence
<220> FEATURE:
<223> OTHER INFORMATION: Synthetic DNA

<400> SEQUENCE: 7
acgccagggt tttcccagtc ac                                              22

<210> SEQ ID NO 8
<211> LENGTH: 22
<212> TYPE: DNA
<213> ORGANISM: Artificial sequence
<220> FEATURE:
<223> OTHER INFORMATION: Synthetic DNA

<400> SEQUENCE: 8
ccagcaccct aagccgacta gg                                              22

<210> SEQ ID NO 9
<211> LENGTH: 21
<212> TYPE: DNA
<213> ORGANISM: Artificial sequence
<220> FEATURE:
<223> OTHER INFORMATION: Synthetic DNA

```
<400> SEQUENCE: 9
acggtgctga tgaagtggat g                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic DNA

<400> SEQUENCE: 10
accacgccca ctaacagttt g                                              21

<210> SEQ ID NO 11
<211> LENGTH: 32
<212> TYPE: DNA
<213> ORGANISM: Artificial sequence
<220> FEATURE:
<223> OTHER INFORMATION: Synthetic DNA

<400> SEQUENCE: 11 gggggggtacc ctggatggcg gcgttagtat cg                                 32

<210> SEQ ID NO 12
<211> LENGTH: 32
<212> TYPE: DNA
<213> ORGANISM: Artificial sequence
<220> FEATURE:
<223> OTHER INFORMATION: Synthetic DNA

<400> SEQUENCE: 12 gggggggtacc tcacagtcgc gttgaattgt cc                                 32

<210> SEQ ID NO 13
<211> LENGTH: 24
<212> TYPE: DNA
<213> ORGANISM: Artificial sequence
<220> FEATURE:
<223> OTHER INFORMATION: Synthetic DNA

<400> SEQUENCE: 13
ccaaggcagc ggtacatcaa gtag                                           24

<210> SEQ ID NO 14
<211> LENGTH: 23
<212> TYPE: DNA
<213> ORGANISM: Artificial sequence
<220> FEATURE:
<223> OTHER INFORMATION: Synthetic DNA

<400> SEQUENCE: 14
tgcacatgtt gtccatcaag atg                                            23

<210> SEQ ID NO 15
<211> LENGTH: 24
<212> TYPE: DNA
<213> ORGANISM: Artificial sequence
<220> FEATURE:
<223> OTHER INFORMATION: Synthetic DNA

<400> SEQUENCE: 15
ggaaacagct atgacatgat tacg                                           24

<210> SEQ ID NO 16
```

```
<211> LENGTH: 23
<212> TYPE: DNA
<213> ORGANISM: Artificial sequence
<220> FEATURE:
<223> OTHER INFORMATION: Synthetic DNA

<400> SEQUENCE: 16
gtagcgaaat catgtattgc acc                                              23

<210> SEQ ID NO 17
<211> LENGTH: 18215
<212> TYPE: DNA
<213> ORGANISM: Artificial sequence
<220> FEATURE:
<223> OTHER INFORMATION: Synthetic DNA

<400> SEQUENCE: 17
ggccaagatg gccgatctgc attttcata ataatcctcg gtactttcta caagatcaat        60
taaattccaa tcaaaaatcg tcttttgcaa gattttgaag tcacagtact tttcattttc      120
aatgtcaaca gcgccccatt tgtattgtct tcctttaact ttttcgccct tttcattaaa      180
aatgtactca ttagatgcaa ttatactgaa tggatatttt tgaaaaatat cttgtgttgc      240
attcaaaact tcatcgccga aaagaaaca tacagggata tcttgtactc ttattatttc       300
tctaacttgt gttttgaagt tttcaattc ctctttcgtt agcaaatctg atttagcaat       360
aaccgggatt aaattcactc tcttcgctaa ttttttcatt gttacgacgt ctaaagtatc      420 aattcccta tttgaaggtc tcagaaagta caaacaacaa tggactctat tatcaaccat       480
ttttgtccta tcaggttgtt cttcttggaa aatgtacgat cttatttctt catcaatata      540
gtttctagac tgcagcccgg gatccgtcga caagcttgtg gagaggtgac ttcatgaacc      600
aagtgtctgt cgatatacaa caaaaggaa ccatttttcat cttgatggac aacatgtgca     660
tcaaaaccct tatcgtaaag agttcttgga cccttggatg gagtgtaaac catgatttaa      720
aacagcaaat aataaaaatc gatagcgaca aaaactgtca atttcaatat tctttatatt      780
tgttgactgc ttagatattt tgagaaaatt cagcggaaac agcgtgatga gtgagttaag      840
ttctgctgtt taaataagta ttcaactact attgaagccg actcatgaag ccggttacgg      900 acaaaccgg gcaaatttcg ccggtcccgg aattttcgtt tccgcaataa agaaccgct        960 catcatcata gcgccagggt agtatactat agaaggtcag actaaactga gtcatctaga     1020
gtaatgacgc ttagtagct tttacatctt cataagaaaa ggaaacttgt agaatggcct      1080
ggcgatttgt ttgctttctt gtgatgaaga aatttcgatg cgattaaccg gcaaaatcag     1140
taaaggtatt tcgcggaggc ggccttcaat catcgaatac tacgtcttaa tatgatgtac     1200
tgtggttcat attttcaagt agtgttagta aatttgtata cgttcatgta agtgtgtatc     1260
ttgagtgtct gtatgggcgc ataaacgtaa gcgagacttc caaatggagc aaacgagaag    1320
agatctttaa agtattatag aagagctggg caggaactat tatgacgtaa agccttgacc    1380
ataataaaga cgattctttg tccctctata caaacatctt gcaagataca caatatttt    1440 caaatcctac tcaataaaaa attaatgaat aaattagtgt gtgtgcatta tatatattaa    1500
aaattaagaa ttagactaaa taagtgtttt ctaaaaaaat attaaagttg aaatgtgcgt    1560
gttgtgaatt gtgctctatt agaataatta tgacttgtgt gcgtttcata ttttaaaata   1620
ggaaataacc aagaaagaaa aagtaccatc cagagaaacc aattatatca aatcaaataa    1680
aacaaccagc ttcggtgtgt gtgtgtgtgt gaagctaaga gttgatgcca tttaatctaa    1740
aaattttaag gtgtgtgtgt ggataaaata ttagaatgac aattcgaatt gcgtacctta    1800
```

```
gtcaaaaaat tagccttttta attctgctgt aacccgtaca tgcccaaaat agggggcggg    1860
ttacacagaa tatataacat cgtaggtgtc tgggtgaaca gtttattcct ggcatccact    1920
aaatataatg gagcccgctt tttaagctgg catccagaaa aaaaagaat cccagcacca     1980 aaatattgtt ttcttcacca accatcagtt cataggtcca ttctcttagc gcaactacag    2040
agaacagggg cacaaacagg caaaaacgg gcacaacctc aatggagtga tgcaacctgc     2100
ctggagtaaa tgatgacaca aggcaattga cccacgcatg tatctatctc attttcttac    2160
accttctatt accttctgct ctctctgatt tggaaaaagc tgaaaaaaaa ggttgaaacc    2220
agttccctga aattattccc ctacttgact aataagtata taaagacggt aggtattgat    2280
tgtaattctg taaatctatt tcttaaactt cttaaattct acttttatag ttagtctttt    2340
ttttagtttt aaaacaccaa gaacttagtt tcgaataaac acacataaac aaacaaaatg    2400
ttatcagtac ctgattatga gttttggttt gttaccggtt cacaacacct ttatggtgaa    2460
gaacaattga agtctgttgc taaggatgcg caagatattg cggataaatt gaatgcaagc    2520
ggcaagttac cttataaagt agtctttaag gatgttatga cgacggctga agtatcacc     2580 aactttatga agaagttaa ttacaatgat aaggtagccg gtgttattac ttggatgcac     2640
acattctcac cagctaagaa ctggattcgt ggaactgaac tgttacaaaa accattatta    2700
cacttagcaa cgcaatattt gaataatatt ccatatgcag acattgactt tgattacatg    2760
aaccttaacc aaagtgccca tggcgaccgc gagtatgcct acattaacgc ccggttgcag    2820
aaacataata agattgttta cggctattgg ggcgatgaag atgtgcaaga gcagattgca    2880
cgttgggaag acgtcgccgt agcgtacaat gagagcttta agttaaggt tgctcgcttt     2940 ggcgacacaa tgcgtaatgt ggccgttact gaaggtgaca aggttgaggc tcaaattaag    3000
atgggctgga cagttgacta ttatggtatc ggtgacttag ttgaagagat caataaggtt    3060
tcggatgctg atgttgataa ggaatacgct gacttggagt ctcggtatga aatggtccaa    3120
ggtgataacg atgcggacac gtataaacat tcagttcggg ttcaattggc acaatatctg    3180
ggtattaagc ggttcttaga aagaggcggt tacacagcct ttaccacgaa ctttgaagat    3240
cttttgggga tggagcaatt acctggtcta gcttcacaat tattaattcg tgatgggtat    3300
ggttttggtg ctgaaggtga ctggaagacg gctgctttag gacgggttat gaagattatg    3360
tctcacaaca agcaaaccgc ctttatgaaa gactacacgt tagacttgcg tcatggtcat    3420
gaagcgatct taggttcaca catgttggaa gttgatccgt ctatcgcaag tgataaacca    3480
cgggtcgaag ttcatccatt ggatattggg ggtaaagatg atcctgctcg cctagtatt     3540 actggttcag aaggtgaagc aattgatgtc accgttgccg atttccgtga tgggttcaag    3600
atgattagct acgcggtaga tgcgaataag ccagaagccg aaacacctaa tttaccagtt    3660
gctaagcaat tatggacccc aaagatgggc ttaaagaaag gtgcactaga atggatgcaa    3720
gctggtggtg tcaccacac gatgctgtcc ttctcgttaa ctgaagaaca aatggaagac    3780
tatgcaacca tggttggcat gactaaggca ttcttaaagt aagtgaattt actttaaatc    3840
ttgcatttaa ataaattttc tttttatagc tttatgactt agtttcaatt tatatactat    3900
tttaatgaca ttttcgattc attgattgaa agctttgtgt ttttttcttga tgcgctattg    3960 cattgttctt gtcttttttcg ccacatgtaa tatctgtagt agatacctga tacattgtgg    4020
atgctgagtg aaatttttagt taataatgga ggcgctctta ataatttttgg ggatattggc    4080 ttttttttttt aaagtttaca aatgaatttt ttccgccagg atcgtacgcc gcggaaccgc    4140
```

```
cagatattca ttacttgacg caaaagcgtt tgaaataatg acgaaaaaga aggaagaaaa      4200
aaaaagaaaa ataccgcttc taggcgggtt atctactgat ccgagcttcc actaggatag      4260
cacccaaaca cctgcatatt tggacgacct ttacttacac caccaaaaac cactttcgcc      4320
tctcccgccc ctgataacgt ccactaattg agcgattacc tgagcggtcc tcttttgttt      4380
gcagcatgag acttgcatac tgcaaatcgt aagtagcaac gtctcaaggt caaaactgta      4440
tggaaacctt gtcacctcac ttaattctag ctagcctacc ctgcaagtca agaggtctcc      4500
gtgattccta gccacctcaa ggtatgcctc tccccggaaa ctgtggcctt ttctggcaca      4560
catgatctcc acgatttcaa catataaata gcttttgata atggcaatat taatcaaatt      4620
tattttactt ctttcttgta acatctctct tgtaatccct tattccttct agctattttt      4680
cataaaaaac caagcaactg cttatcaaca cacaaacact aaatcaaaat gaatttagtt      4740
gaaacagccc aagcgattaa aactggcaaa gtttctttag gaattgagct tggctcaact      4800
cgaattaaag ccgttttgat cacggacgat tttaatacga ttgcttcggg aagttacgtt      4860
tgggaaaacc aatttgttga tggtacttgg acttacgcac ttgaagatgt ctggaccgga      4920
attcaacaaa gttatacgca attagcagca gatgtccgca gtaaatatca catgagtttg      4980
aagcatatca atgctattgg cattagtgcc atgatgcacg ataccctagc atttgatcaa      5040
caagcgaaat tattagttcc gtttcggact tggcgtaata acattacggg gcaagcagca      5100
gatgaattga ccgaattatt tgatttcaac attccacaac ggtggagtat cgcacactta      5160
taccaggcaa tcttaaataa tgaagcgcac gttaaacagg tggacttcat aacaacgctg      5220
gctggctatg taacctggaa attgtcgggt gagaaagttc taggaatcgg tgatgcgtct      5280
ggcgttttcc caattgatga aacgactgac acatacaatc agacgatgtt aaccaagttt      5340
agccaacttg acaaagttaa accgtattca tgggatatcc ggcatatttt accgcgggtt      5400
ttaccagcgg gagccattgc tggaaagtta acggctgccg gggcgagctt acttgatcag      5460
agcggcacgc tcgacgctgg cagtgttatt gcaccgccag aaggggatgc tggaacagga      5520
atggtcggta cgaacagcgt ccgtaaacgc acgggtaaca tctcggtggg aacctcagca      5580
ttttcgatga acgttctaga taaaccattg tctaaagtct atcgcgatat tgatattgtt      5640
atgacgccag atgggtcacc agttgcaatg gtgcatgtta ataattgttc atcagatatt      5700
aatgcgtggg caacgatttt tcatgagttt gcagcccggt tgggaatgga attgaaaccg      5760
gatcgattat atgaaacgtt attcttggaa tcaactcgcg ctgatgcgga tgctggaggg      5820
ttggctaatt atagttatca atccggtgag aatattacta agattcaagc tggtcggccg      5880
ctatttgtac ggacaccaaa cagtaaattt agtttaccga actttatgtt gactcaatta      5940
tatgcggcgt tcgcaccccct ccaacttggt atggatattc ttgttaacga agaacatgtt      6000
caaacggacg ttatgattgc acagggtgga ttgttccgaa cgccggtaat tggccaacaa      6060
gtattggcca acgcactgaa cattccgatt actgtaatga gtactgctgg tgaaggcggc      6120
ccatggggga tggcagtgtt agccaacttt gcttgtcggc aaactgcaat gaacctagaa      6180
gatttcttag atcaagaagt ctttaaagag ccagaaagta tgacgttgag tccagaaccg      6240
gaacgggtgg ccggatatcg tgaatttatt caacgttatc aagctggctt accagttgaa      6300
gcagcggctg ggcaagcaat caaatattag agcttttgat taagccttct agtccaaaaa      6360
acacgttttt ttgtcatttta tttcattttc ttagaatagt ttagtttatt cattttatag      6420
tcacgaatgt tttatgattc tatatagggt tgcaaacaag cattttttcat tttatgttaa      6480 aacaatttca ggtttacctt ttattctgct tgtggtgacg cgggtatccg cccgctcttt      6540
```

```
tggtcaccca tgtatttaat tgcataaata attcttaaaa gtggagctag tctatttcta    6600
tttacatacc tctcatttct catttcctcc actagtagaa aattttgcca tcggacatgc    6660
taccttacgc ttatatctct cattggaata tcgttttctg attaaaacac ggaagtaaga    6720
acttaattcg tttttcgttg aactatgttg tgccagcgta acattaaaaa agagtgtaca    6780
aggccacgtt ctgtcaccgt cagaaaaata tgtcaatgag gcaagaaccg ggatggtaac    6840
aaaaatcacg atctgggtgg gtgtgggtgt attggattat aggaagccac gcgctcaacc    6900
tggaattaca ggaagctggt aattttttgg gtttgcaatc atcaccatct gcacgttgtt    6960
ataatgtccc gtgtctatat atatccattg acggtattct attttttttgc tattgaaatg    7020
agcgtttttt gttactacaa ttggttttac agacggaatt ttccctattt gtttcgtccc    7080
attttttcctt ttctcattgt tctcatatct taaaaaggtc cttcttcat aatcaatgct    7140
ttcttttact taatatttta cttgcattca gtgaatttta atacatattc ctctagtctt    7200
gcaaaatcga tttagaatca agataccagc ctaaaaatgc tagaagcatt aaaacaagaa    7260
gtttatgagg ctaacatgca gcttccaaag ctgggcctgg ttacttttac ctggggcaat    7320
gtctcgggca ttgaccggga aaaaggccta ttcgtgatca agccatctgg tgttgattat    7380
ggtgaattaa aaccaagcga tttagtcgtt gttaacttac agggtgaagt ggttgaaggt    7440
aaactaaatc cgtctagtga tacgccgact catacggtgt tatataacgc ttttcctaat    7500
attggcggaa ttgtccatac tcattcgcca tgggcagttg cctatgcagc tgctcaaatg    7560
gatgtgccag ctatgaacac gacccatgct gatacgttct atggtgacgt gccggccgcg    7620
gatgcgctga ctaaggaaga aattgaagca gattatgaag gcaacacggg taaaaccatt    7680
gtgaagacgt tccaagaacg gggcctcgat tatgaagctg taccagcctc attagtcagc    7740
cagcacggcc catttgcttg gggaccaacg ccagctaaag ccgtttacaa tgctaaagtg    7800
ttggaagtgg ttgccgaaga agattatcat actgcgcaat tgacccgtgc aagtagcgaa    7860
ttaccacaat atttattaga taagcattat ttacgtaagc atggtgcaag tgcctattat    7920
ggtcaaaata atgcgcattc taaggatcat gcagttcgca agtaaacaaa tcgctcttaa    7980
atatatacct aaagaacatt aaagctatat tataagcaaa gatacgtaaa ttttgcttat    8040
attattatac acatatcata tttctatatt tttaagattt ggttatataa tgtacgtaat    8100
gcaaaggaaa taaattttat acattattga acagcgtcca gtaactaca ttatgtgcac    8160
taatagttta gcgtcgtgaa gactttattg tgtcgcgaaa agtaaaaatt ttaaaaatta    8220
gagcaccttg aacttgcgaa aaaggttctc atcaactgtt taaaaacgcg tgtcttctgt    8280
gtttcagttc agggcttttc ggaggatgtg aatcgacggc gtactgtcct tgggaacttt    8340
gtctacgtat tttcacttcc tcagcgaatc cagagactat cttgggaaat tcgacaggac    8400
agtctgttga caaccgactc ccttttgact tcataataaa aattcaatga cgcaaaagga    8460
attttaggtt tttattattt atttatttat ttctgttaat tgatcctttt ctttccacta    8520
ccaacaacaa aaagggggg aaaagatgt ataatctaaa agacactaat ctgctcttga    8580
tatccttatt atgtaatgga ataactcata taaatgtaaa atagaacttc aaattaatat    8640
tataatgata gtcgaggtca gacacactta aatacatta agtaaagaaa aaaaaatgtc    8700
tgtcatcgag gtctcttttg tgtcgctaac aaaacatcac taaatacgaa gacactttgc    8760
atgggaagga tgcagcaaat ggcaaactaa cgggccattg attggtttac ctcttctatt    8820
tgtattacga ccagaaagaa cgaatggttt tcatcaatga ggtaggaaac gacctaaata    8880
```

```
taatgtagca tagataaaat ctttgtactg tatggttgca atgccttctt gattagtatc    8940
gaatttcctg aataattttg ttaatctcat tagccaaact aacgcctcaa cgaatttatc    9000
aaactttagt tcttttcctg ttccatttct gtttataaac tcagcatatt ggtcaaatgt    9060
tttctcgcta acttcaaaag gtattagata tcctagttct tgaagtgagt tatgaaattc    9120
gcttacagaa atggtgagcg atccgttgat atcattgtcc acataaactt ttctccaact    9180
tttcactctt ttgtataggg cgatgaattc tgcctggttg acagtgccaa acctggaagc    9240
accaaataaa tttatcagcg catctactga tgatatacaa aaatgggagt tgtcgtcgtt    9300
ttgtagtaag ttctgtagtt cctcagctgt cagtcggttt ttgccctttta catcatggtt    9360
atgaaatagc tgtgtggcca cttgcatgtc tcgtacatct tctctgctat cgaacgaagc    9420
aggtgcaact ttcttcaaga gttgtgcagg cactgcttga ttgtgaatta ggggaggagg    9480
agaggaagct atccgttgag cggaagtgtt caagttgtta taatgggttg gcgctggagg    9540
tataggcctg cctgctggtt tctgtgcgat aacattatat ctaggatcca caggtgtttt    9600
cgtatgtctt ggagaataac tttggggaga accataggag tggtgaccgt tttctgctct    9660
gttttttgtta tattgagttt gtaagggaat tggagctgag tggactctag tgttgggagt    9720
ttgtgcttga gtaaccggta ccacggctcc tcgctgcaga cctgcgagca gggaaacgct    9780
cccctcacag tcgcgttgaa ttgtccccac gccgcgcccc tgtagagaaa tataaaggt    9840
taggatttgc cactgaggtt cttctttcat atacttcctt ttaaaatctt gctaggatac    9900
agttctcaca tcacatccga acataaacaa ccatgggtaa ggaaaagact cacgtttcga    9960
ggccgcgatt aaattccaac atggatgctg atttatatgg gtaaaatgg gctcgcgata    10020
atgtcgggca atcaggtgcg acaatctatc gattgtatgg aagcccgat gcgccagagt    10080
tgtttctgaa acatggcaaa ggtagcgttg ccaatgatgt tacagatgag atggtcagac    10140
taaactggct gacggaattt atgcctcttc cgaccatcaa gcattttatc cgtactcctg    10200
atgatgcatg gttactcacc actgcgatcc ccggcaaaac agcattccag gtattagaag    10260
aatatcctga ttcaggtgaa aatattgttg atgcgctggc agtgttcctg cgccggttgc    10320
attcgattcc tgtttgtaat tgtcctttta acagcgatcg cgtatttcgt ctcgctcagg    10380
cgcaatcacg aatgaataac ggtttggttg atgcgagtga ttttgatgac gagcgtaatg    10440
gctggcctgt tgaacaagtc tggaaagaaa tgcataagct tttgccattc tcaccggatt    10500
cagtcgtcac tcatggtgat ttctcacttg ataaccttat ttttgacgag gggaaattaa    10560
taggttgtat tgatgttgga cgagtcggaa tcgcagaccg ataccaggat cttgccatcc    10620
tatggaactg cctcggtgag ttttctcctt cattacagaa acggcttttt caaaaatatg    10680
gtattgataa tcctgatatg aataaattgc agtttcattt gatgctcgat gagttttttct    10740
aatcagtact gacaataaaa agattcttgt tttcaagaac ttgtcatttg tatagttttt    10800
ttatattgta gttgttctat tttaatcaaa tgttagcgtg atttatattt ttttcgcct    10860
cgacatcatc tgcccagatg cgaagttaag tgcgcagaaa gtaatatcat gcgtcaatcg    10920
tatgtgaatg ctggtcgcta tactgctgtc gattcgatac taacgccgcc atccagggta    10980
ccatcctttt gttgtttccg ggtgtacaat atggacttcc tcttttctgg caaccaaacc    11040
catacatcgg gattcctata ataccttcgt tggtctccct aacatgtagg tggcggaggg    11100
gagatataca atagaacaga taccagacaa gacataatgg gctaaacaag actacaccaa    11160
ttacactgcc tcattgatgg tggtacataa cgaactaata ctgtagccct agacttgata    11220
gccatcatca tatcgaagtt tcactaccct ttttccattt gccatctatt gaagtaataa    11280
```

```
taggcgcatg caacttcttt tctttttttt tcttttctct ctcccccgtt gttgtctcac   11340
catatccgca atgacaaaaa aaatgatgga agacactaaa ggaaaaaatt aacgacaaag   11400
acagcaccaa cagatgtcgt tgttccagag ctgatgaggg gtatcttcga acacacgaaa   11460
ctttttcctt ccttcattca cgcacactac tctctaatga gcaacggtat acggccttcc   11520
ttccagttac ttgaatttga ataaaaaaa gtttgccgct ttgctatcaa gtataaatag    11580
acctgcaatt attaatcttt tgtttcctcg tcattgttct cgttcccttt cttccttgtt   11640 tcttttctg cacaatattt caagctatac caagcataca atcaactatc tcatatacaa    11700
tgcctcaatc ctgggaagaa ctggccgctg ataagcgcgc ccgcctcgca aaaccatcc    11760 ctgatgaatg gaaagtccag acgctgcctg cggaagacag cgttattgat ttcccaaaga   11820
aatcggggat cctttcagag gccgaactga agatcacaga ggcctccgct gcagatcttg   11880
tgtccaagct ggcggccgga gagttgacct cggtggaagt tacgctagca ttctgtaaac   11940
gggcagcaat cgcccagcag ttaacaaact gcgcccacga gttcttccct gacgccgctc   12000
tcgcgcaggc aagggaactc gatgaatact acgcaaagca caagagaccc gttggtccac   12060
tccatggcct ccccatctct ctcaaagacc agcttcgagt caagggctac gaaacatcaa   12120
tgggctacat ctcatggcta aacaagtacg acgaagggga ctcggttctg acaaccatgc   12180
tccgcaaagc cggtgccgtc ttctacgtca agacctctgt cccgcagacc ctgatggtct   12240
gcgagacagt caacaacatc atcgggcgca ccgtcaaccc acgcaacaag aactggtcgt   12300
gcggcggcag ttctggtggt gagggtgcga tcgttgggat tcgtggtggc gtcatcggtg   12360
taggaacgga tatcggtggc tcgattcgag tgccggccgc gttcaacttc ctgtacggtc   12420
taaggccgag tcatgggcgg ctgccgtatg caaagatggc gaacagcatg gagggtcagg   12480
agacggtgca cagcgttgtc gggccgatta cgcactctgt tgaggacctc cgcctcttca   12540
ccaaatccgt cctcggtcag gagccatgga aatacgactc caaggtcatc cccatgccct   12600
ggcgccagtc cgagtcggac attattgcct ccaagatcaa gaacggcggg ctcaatatcg   12660
gctactacaa cttcgacggc aatgtccttc cacaccctcc tatcctgcgc ggcgtggaaa   12720
ccaccgtcgc cgcactcgcc aaagccggtc acaccgtgac cccgtggacg ccatacaagc   12780
acgatttcgg ccacgatctc atctcccata tctacgcggc tgacggcagc gccgacgtaa   12840
tgcgcgatat cagtgcatcc ggcgagccgg cgattccaaa tatcaaagac ctactgaacc   12900
cgaacatcaa agctgttaac atgaacgagc tctgggacac gcatctccag aagtggaatt   12960
accagatgga gtaccttgag aaatggcggg aggctgaaga aaaggccggg aaggaactgg   13020
acgccatcat cgcgccgatt acgcctaccg ctgcggtacg gcatgaccag ttccggtact   13080
atgggtatgc ctctgtgatc aacctgctgg atttcacgag cgtggttgtt ccggttacct   13140
ttgcggataa gaacatcgat aagaagaatg agagtttcaa ggcggttagt gagcttgatg   13200
ccctcgtgca ggaagagtat gatccggagg cgtaccatgg ggcaccggtt gcagtgcagg   13260
ttatcggacg gagactcagt gaagagagga cgttggcgat tgcagaggaa gtgggggaagt   13320 tgctgggaaa tgtggtgact ccataggtcg agaatttata cttagataag tatgtactta   13380
caggtatatt tctatgagat actgatgtat acatgcatga taatatttaa acggttatta   13440
gtgccgattg tcttgtgcga taatgacgtt cctatcaaag caatacactt accacctatt   13500
acatgggcca agaaaatatt ttcgaacttg tttagaatat tagcacagag tatatgatga   13560
tatccgttag attatgcatg attcattcct acaacttttt cgtagcataa ggattaatta   13620
```

```
cttggatgcc aataaaaaaa aaaaacatcg agaaaatttc agcatgctca gaaacaattg   13680
cagtgtatca aagtaaaaaa aagattttcg ctacatgttc cttttgaaga aagaaaatca   13740
tggaacatta gatttacaaa aatttaacca ccgctgatta acgattagac cgttaagcgc   13800
acaacaggtt attagtacag agaaagcatt ctgtggtgtt gccccggact ttcttttgcg   13860
acataggtaa atcgaatacc atcatactat cttttccaat gactccctaa agaaagactc   13920
ttcttcgatg ttgtatacgt tggagcatag ggcaagaatt gtggcttgag atctagatta   13980
cgtggaagaa aggtagtaaa agtagtagta taagtagtaa aaagaggtaa aaagagaaaa   14040
ccggctacat actagagaag cacgtacaca aaaactcata ggcacttcat catacgacag   14100
tttcttgatg cattataata gtgtattaga tattttcaga aatatgcata gaacctcttc   14160
ttgcctttac tttttataca tagaacattg gcagatttac ttacactact ttgtttctac   14220
gccatttctt ttgttttcaa cacttagaca agttgttgag aaccggacta ctaaaaagca   14280
atgttcccac tgaaaatcat gtacctgcag gataataacc ccctaattct gcatcgatcc   14340
agtatgtttt tttttctcta ctcattttta cctgaagata gagcttctaa aacaaaaaaa   14400
atcagcgatt acatgcatat tgtgtgttct agaattgcgg atcaccagat cgccattaca   14460
atgtatgcag gcaaatattt ctcagaatga aaaatagaga aaggaaacg aaaattctgt   14520 aagatgcctt cgaagagatt tctcgatatg caaggcgtgc atcagggtga tccaaaggaa   14580
ctcgagagag agggcgaaag gcaatttaat gcattgcttc tccattgact tctagttgag   14640
cggataagtt cggaaatgta agtcacagct aatgacaaat ccactttagg tttcgaggca   14700
ctatttaggc aaaaagacga gtggggaaat aacaaacgct caaacatatt agcatatacc   14760
ttcaaaaaat gggaatagta tataaccttc cggttcgtta ataaatcaaa tctttcatct   14820
agttctctta agatttcaat attttgcttt cttgaagaaa gaatctactc tcctccccca   14880
ttcgcactgc aaagctagct tggcactggc cgtcgtttta caacgtcgtg actgggaaaa   14940
ccctggcctt acccaactta atcgccttgc agcacatccc cctttcgcca gctgcgtaa   15000 tagcgaagag gcccgcaccg atcgcccttc ccaacagttg cgcagcctga atggcgaatg   15060
ggaaattgta aacgttaata ttttgttaaa attcgcgtta aattttttgtt aaatcagctc   15120 attttttaac caataggccg aaatcggcaa aatcccttat aaatcaaaag aatagaccga   15180
gatagggttg agtgttgttc cagttttgaa caagagtcca ctattaaaga acgtggactc   15240
caacgtcaaa gggcgaaaaa ccgtctatca gggcgatggc ccactacgtg aaccatcacc   15300
ctaatcaagt tttttggggt cgaggtgccg taaagcacta atcggaacc ctaaagggag   15360 cccccgattt agagcttgac ggggaaagcc ggcgaacgtg gcgagaaagg aagggaagaa   15420
agcgaaagga gcgggcgcta gggcgctggc aagtgtagcg gtcacgctgc gcgtaaccac   15480
cacacccgcc gcgcttaatg cgccgctaca gggcgcgtca ggtggcactt tcggggaaa   15540 tgtgcgcgga accccctattt gtttatttt ctaaatacat tcaaatatgt atccgctcat   15600
gagacaataa ccctgataaa tgcttcaata atattgaaaa aggaagagta tgagtattca   15660
acatttccgt gtcgccctta ttccctttt tgcggcattt tgccttcctg tttttgctca   15720
cccagaaacg ctggtgaaag taaaagatgc tgaagatcag ttgggtgcac gagtgggtta   15780
catcgaactg gatctcaaca gcggtaagat ccttgagagt tttcgccccg aagaacgttt   15840
tccaatgatg agcactttta aagttctgct atgtggcgcg gtattatccc gtattgacgc   15900
cgggcaagac caactcggtc gccgcataca ctattctcag aatgacttgg ttgagtactc   15960
accagtcaca gaaaagcatc ttacggatgg catgacagta agagaattat gcagtgctgc   16020
```

```
cataaccatg agtgataaca ctgcggccaa cttacttctg acaacgatcg gaggaccgaa    16080
ggagctaacc gcttttttgc acaacatggg ggatcatgta actcgccttg atcgttggga    16140
accggagctg aatgaagcca taccaaacga cgagcgtgac accacgatgc ctgtagcaat    16200
ggcaacaacg ttgcgcaaac tattaactgg cgaactactt agtctagctt cccggcaaca    16260
attaatagac tggatggagg cggataaagt tgcaggacca cttctgcgct cggcccttcc    16320
ggctggctgg tttattgctg ataaatctgg agccggtgag cgtgggtctc gcggtatcat    16380
tgcagcactg gggccagatg gtaagccctc ccgtatcgta gttatctaca cgacggggag    16440
tcaggcaact atgatgaac gaaatagaca gatcgctgag ataggtgcct cactgattaa    16500
gcattggtaa ctgtcagacc aagtttactc atatatactt tagattgatt taaaacttca    16560
tttttaattt aaaaggatct aggtgaagat cctttttgat aatctcatga ccaaaatccc    16620
ttaacgtgag ttttcgttcc actgagcgtc agaccccgta gaaaagatca aggatcttc    16680 ttgagatcct ttttttctgc gcgtaatctg ctgcttgcaa acaaaaaaac caccgctacc    16740
agcggtggtt tgtttgccgg atcaagagct accaactctt tttccgaagg taactggctt    16800
cagcagagcg cagataccaa atactgtcct tctagtgtag ccgtagttag gccaccactt    16860
caagaactct gtagcaccgc ctacatacct cgctctgcta atcctgttac cagtggctgc    16920
tgccagtggc gataagtcgt gtcttaccgg gttggactca agacgatagt taccggataa    16980
ggcgcagcgg tcgggctgaa cggggggttc gtgcacacag cccagcttgg agcgaacgac    17040
ctacaccgaa ctgagatacc tacagcgtga gcattgagaa agcgccacgc ttcccgaagg    17100
gagaaaggcg gacaggtatc cggtaagcgg cagggtcgga acaggagagc gcacgaggga    17160
gcttccaggg ggaaacgcct ggtatcttta tagtcctgtc gggtttcgcc acctctgact    17220
tgagcgtcga ttttttgtgat gctcgtcagg ggggcggagc ctatggaaaa acgccagcaa    17280
cgcggccttt ttacggttcc tggccttttg ctggccttt gctcacatgt tctttcctgc    17340
gttatcccct gattctgtgg ataaccgtat taccgccttt gagtgagctg ataccgctcg    17400
ccgcagccga acgaccgagc gcagcgagtc agtgagcgag gaagcggaag agcgcccaat    17460
acgcaaaccg cctctccccg cgcgttggcc gattcattaa tgcagctggc acgacaggtt    17520
tcccgactgg aaagcgggca gtgagcgcaa cgcaattaat gtgagttagc tcactcatta    17580
ggcaccccag gctttacact ttatgcttcc ggctcgtatg ttgtgtggaa ttgtgagcgg    17640
ataacaattt cacacaggaa acagctatga catgattacg aatttaatac gactcacaat    17700
agggaattag cttgcgcgaa attattggct tttttttttt tttaattaat actacctttt    17760
gatgtgaacg tttactaaag tagcactatc tgtggaatgg ctgttggaac ttttttccgat    17820 taacagcttg tattccaagt cctgacattc cagttgtaag ttttccaact tgtgattcaa    17880
ttgttcaatc tcttggttaa aattctcttg ttccatgaat aggctctttt tccagtctcg    17940
aaattttgaa atttctctgt tggacagctc gttgaatttt ttcttagctt ctaattgtct    18000
agttataaat tcaggatccc attctgtagc caccttatcc atgaccgttt tattaattat    18060
ttcatagcac ttgtaatttt tgagtttgtt ttcctcgatt tcatcgaagt tcatttcttc    18120
ctccaaaaat ttcctttgtt cttccgttat gtcaacactt ttcgttgtta agcaatctct    18180
ggcctttaat agcctagttc ttagcatttc agatc                              18215

<210> SEQ ID NO 18
<211> LENGTH: 23
<212> TYPE: DNA
```

```
<213> ORGANISM: Artificial sequence
<220> FEATURE:
<223> OTHER INFORMATION: Synthetic DNA

<400> SEQUENCE: 18
tgatcttgta gaaagtaccg agg                                           23

<210> SEQ ID NO 19
<211> LENGTH: 25
<212> TYPE: DNA
<213> ORGANISM: Artificial sequence
<220> FEATURE:
<223> OTHER INFORMATION: Synthetic DNA

<400> SEQUENCE: 19
ctttgttctt ccgttatgtc aacac                                         25

<210> SEQ ID NO 20
<211> LENGTH: 23
<212> TYPE: DNA
<213> ORGANISM: Artificial sequence
<220> FEATURE:
<223> OTHER INFORMATION: Synthetic DNA

<400> SEQUENCE: 20
ttccaagaag aacaacctga tag                                           23

<210> SEQ ID NO 21
<211> LENGTH: 21
<212> TYPE: DNA
<213> ORGANISM: Artificial sequence
<220> FEATURE:
<223> OTHER INFORMATION: Synthetic DNA

<400> SEQUENCE: 21
tgatgtgaac gtttactaaa g                                             21

<210> SEQ ID NO 22
<211> LENGTH: 22
<212> TYPE: DNA
<213> ORGANISM: Artificial sequence
<220> FEATURE:
<223> OTHER INFORMATION: Synthetic DNA

<400> SEQUENCE: 22
tgttcttctt ggaaaatgta cg                                            22

<210> SEQ ID NO 23
<211> LENGTH: 34
<212> TYPE: DNA
<213> ORGANISM: Artificial sequence
<220> FEATURE:
<223> OTHER INFORMATION: Synthetic DNA

<400> SEQUENCE: 23
gattcgcggc cgcctgaact gaaacacaga agac                               34
```

FERMENTATIVE PRODUCTION OF ETHANOL FROM GLUCOSE, GALACTOSE AND ARABINOSE EMPLOYING A RECOMBINANT YEAST STRAIN

CROSS REFERENCE TO RELATED APPLICATIONS

This application is a §371 National Stage Application of PCT/EP2010/059618, filed Jul. 6, 2010, which claims priority to European Application No. 09165229.7 filed Jul. 10, 2009.

BACKGROUND OF THE INVENTION

Field of the Invention

The invention relates to mixed sugar fermentation, in particular the fermentation of a sugar composition comprising glucose, galactose and arabinose. The sugar composition may originate from ligno-cellulosic material.

Description of Related Art

Most of the ethanol produced as alternative for fossil fuels is currently from fermentation of corn starch and sugar cane based sucrose. In order to reach the ambitious goals for producing renewable fuels, new technologies are being developed for converting non-food biomass into fermentation products such as ethanol. *Saccharomyces cerevisiae* is the organism of choice in the ethanol industry, but it cannot utilize five-carbon sugars contained in the hemicellulose component of biomass feedstocks. Hemicellulose can make up to 20-30% of biomass, with xylose and arabinose being the most abundant C5 sugars. Heterologous expression of a xylose isomerase (XI) is an option for enabling yeast cells to metabolize and ferment xylose. Likewise, expression of bacterial genes araA, araB, and araD in *S. cerevisiae* strains results in utilization and efficient alcoholic fermentation of arabinose. Galactose is a C6-sugar that is also a sugar that is often present in lignocellulose, often in amounts (~4% of total sugars) that are not to be neglected for economic reasons.

J. van den Brink et al, Microbiology (2009)155, 1340-1350 discloses that glucose is the favoured carbon source for *Saccharomyces cerevisiae* and that upon switching from glucose limited fermentation conditions to galactose-excess condition under anaerobic condition, galactose was not consumed.

Sofar no process has been disclosed to convert galactose, into the fermentation product in the same process with glucose and one or more C5 sugar. An object of the invention is therefore to provide a process to convert galactose into the fermentation product in the same process with glucose and one or more C5 sugar.

SUMMARY

The present invention provides a process for the production of one or more fermentation products from a sugar composition, comprising the following steps:
a) fermentation of the sugar composition in the presence of a yeast belonging to the genera *Saccharomyces, Kluyveromyces, Candida, Pichia, Schizosaccharomyces, Hansenula, Kloeckera, Schwanniomyces* or *Yarrowia*,: and
b) recovery of the fermentation product,
   wherein the yeast comprises the genes araA, araB and araD and the sugar composition comprises glucose, galactose and arabinose.

Advantageously the sugars glucose, galactose and arabinose are converted into fermentation product.

Preferably the mixed sugar cell is of the genus *Saccharomyces* more preferably a *Saccharomyces cerevisiae*.

The invention further relates to the use of genes araA, araB and araD, to confer, through expression of those genes, on a glucose fermenting strain the ability to anaerobically ferment galactose in the presence of arabinose.

Figure 14:
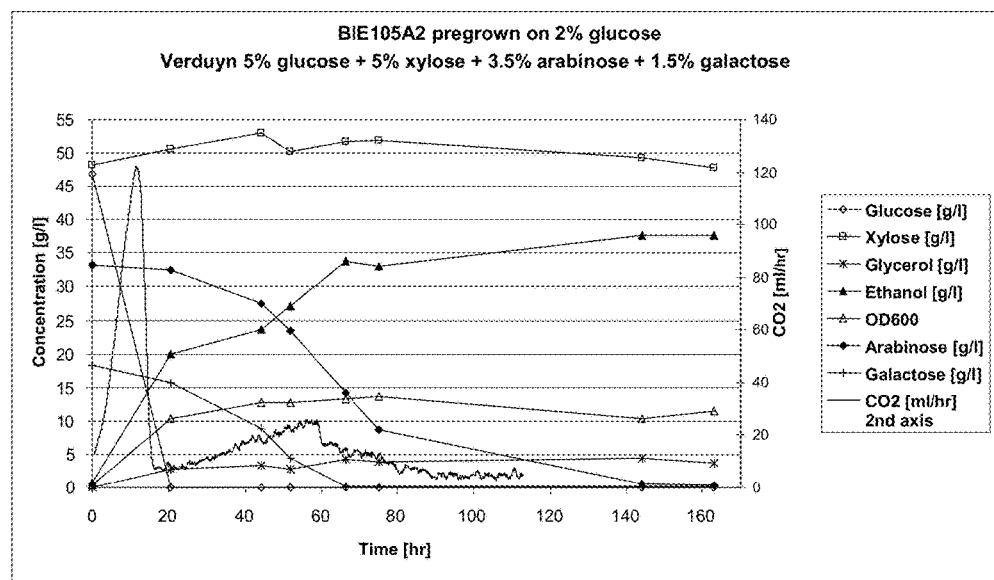

FIG. 14 sets out sugar conversion and product formation of BIE105A2 on synthetic corn fiber model medium. $CO_2$ production was measured constantly. Growth was monitored by following optical density of the culture. Preculture was grown on 2% glucose.

Figure 15:
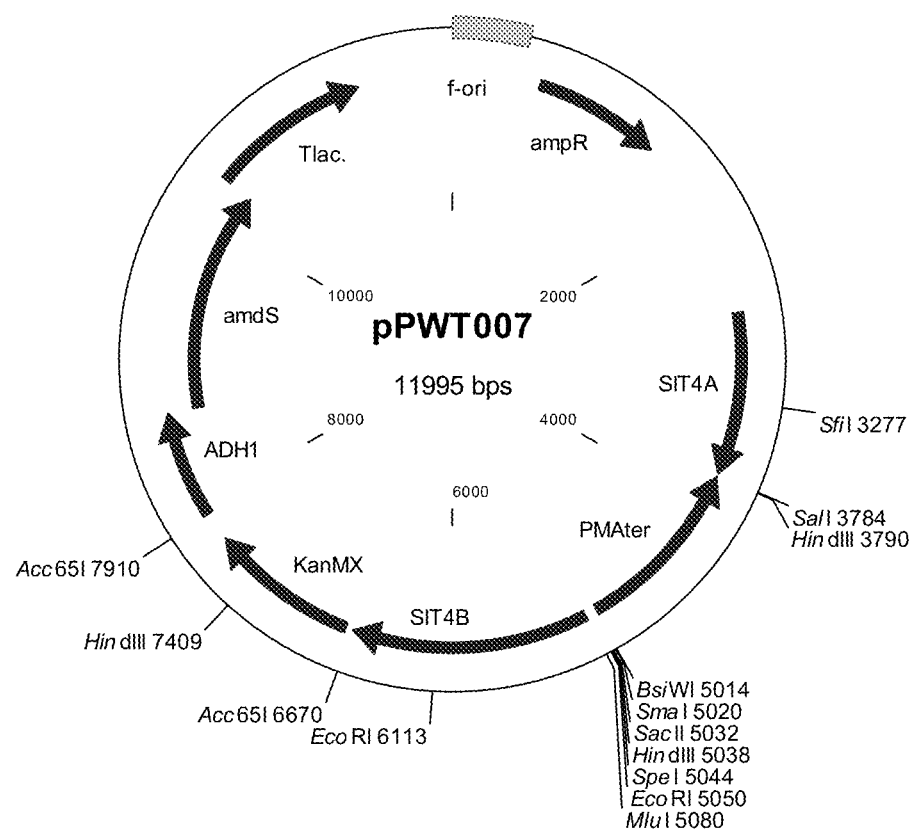

FIG. 15 sets out a physical map of plasmid pPWT007

Figure 16:
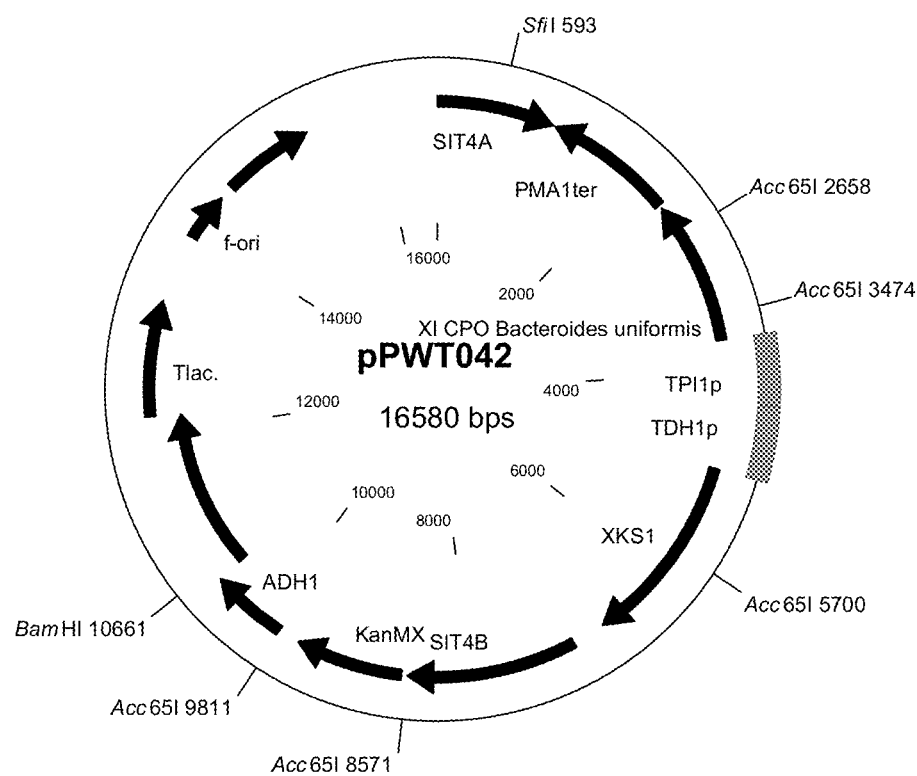

FIG. 16 sets out a physical map of plasmid pPWT042

Figure 17:
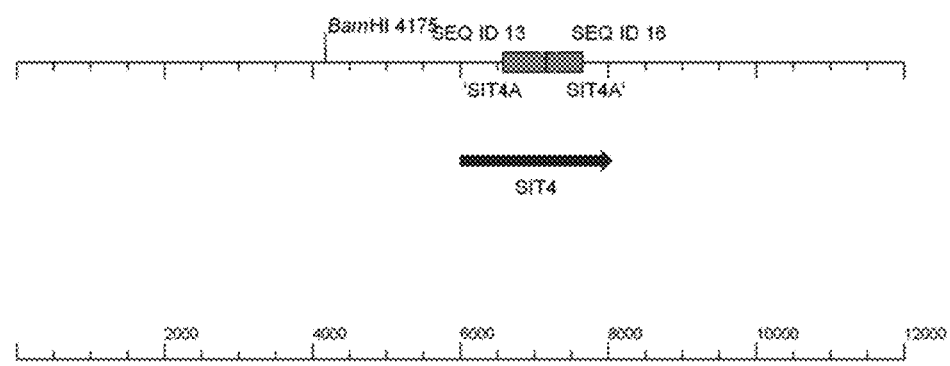
Figure 17:
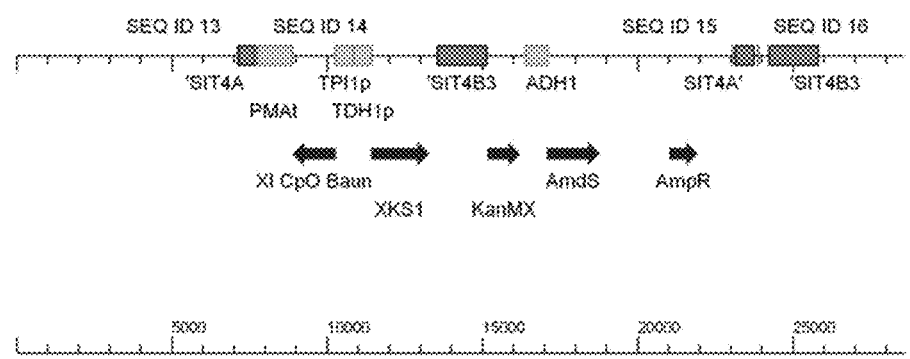

FIG. 17 sets out a physical map of the wild-type SIT4-locus (panel a) and a one copy integration of PWT080 in the SIT4-locus (panel b, showing where the primers bind).

Figure 18:
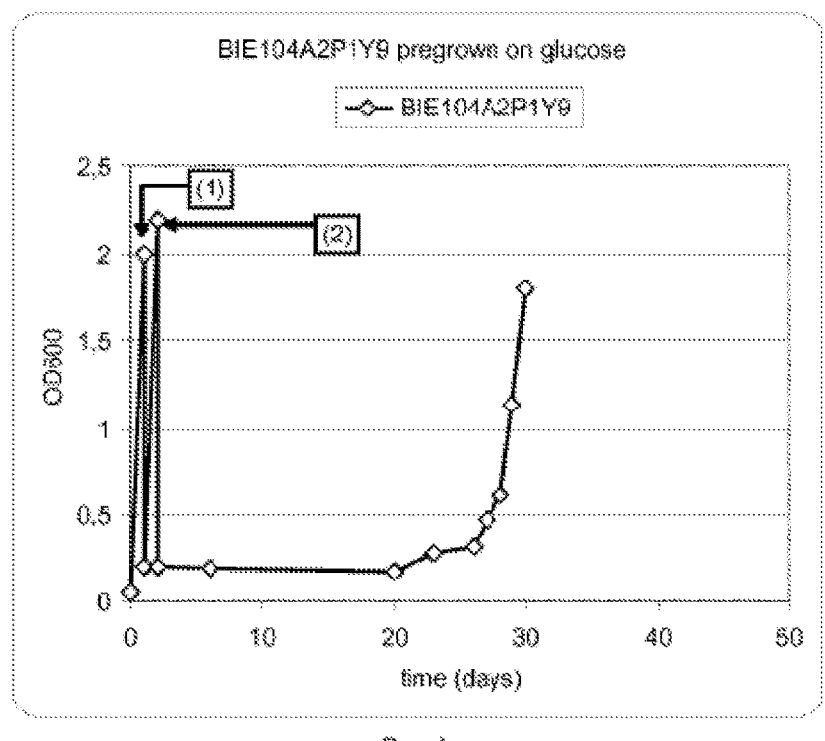
Figure 18:
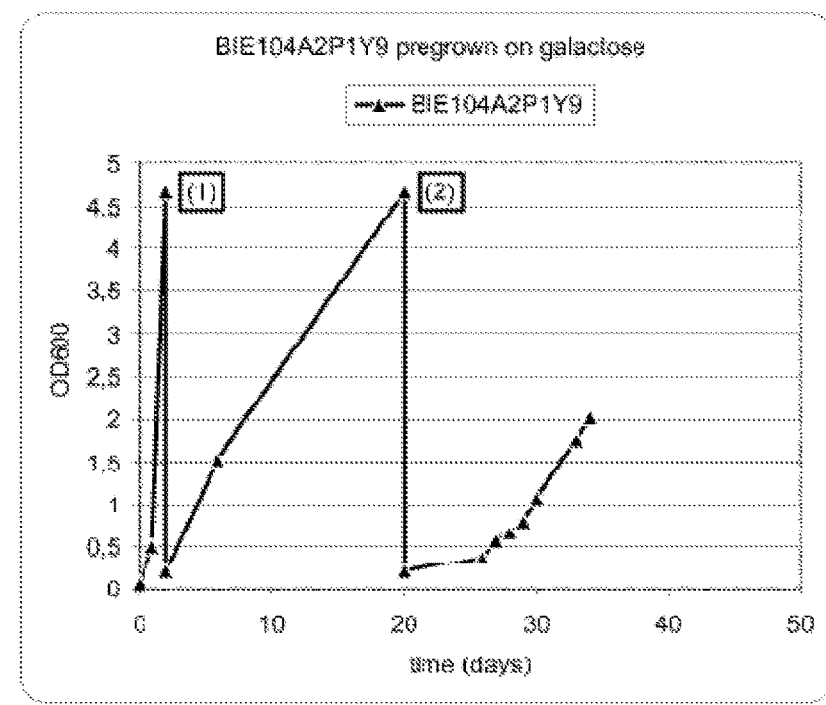

FIG. 18 sets out a graphic representation of growth curves of strain BIE104A2P1Y9 on different media. Panel a: strain BIE104A2P1Y9 grown on glucose, followed by events indicated in the graph by numbers (1) transfer to 1% arabinose+1% xylose and (2) transfer to 2% xylose+0.2% arabinose. Panel b: strain BIE104A2P1Y9 grown on galactose, followed by (1) transfer to 1% arabinose+1% xylose and (2) transfer to 2% xylose+0.2% arabinose.

Figure 19:
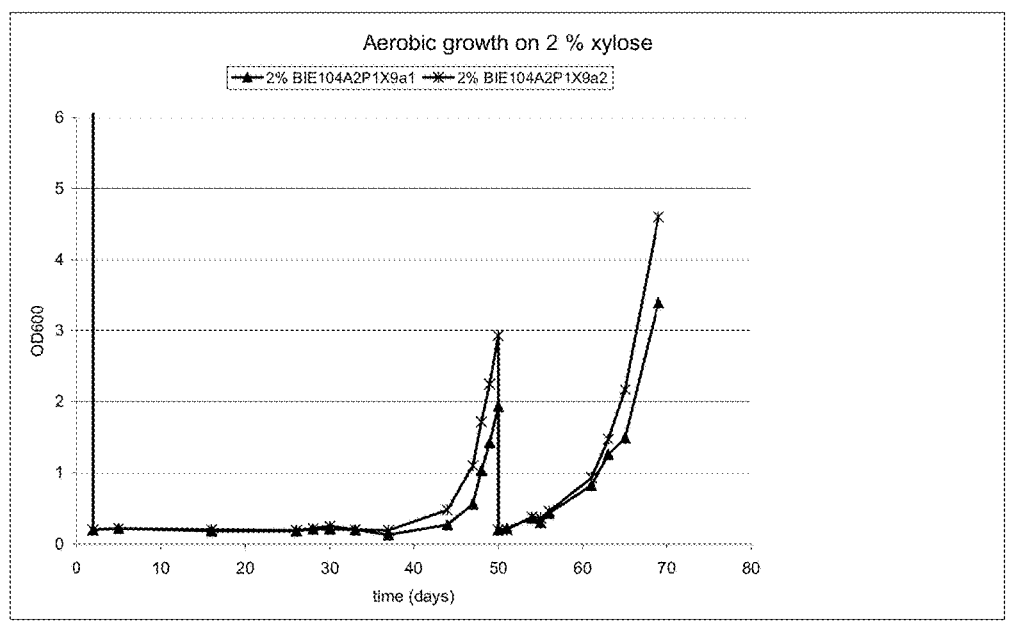

FIG. 19 sets out growth on Verduyn-medium supplemented with 2% xylose of strain BIE104A2P1Y9. Two independent colonies were tested. After reaching on OD 600 of 2, strains were transferred to fresh medium and immediately started to grow again on xylose.

Figure 20:
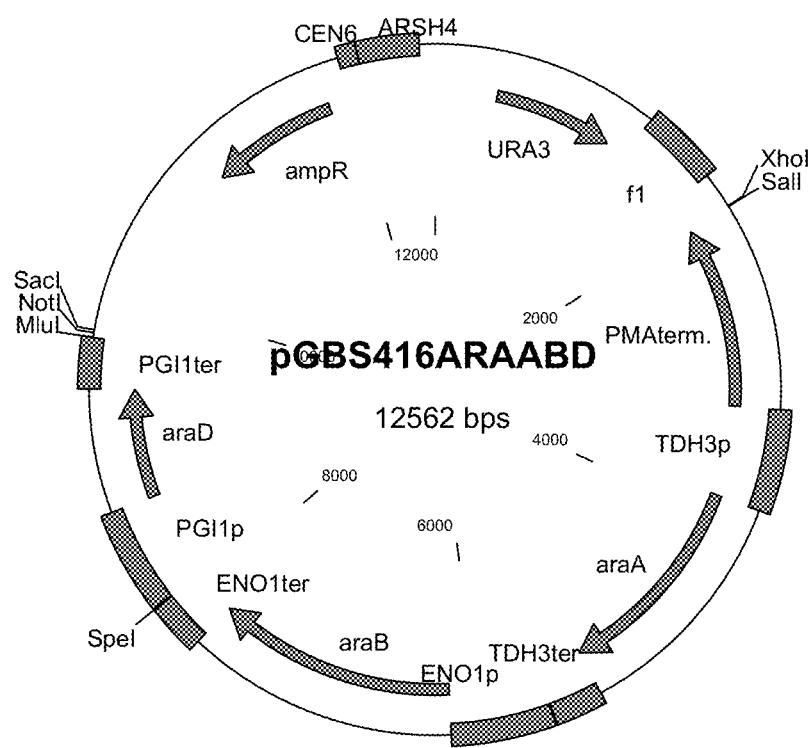

FIG. 20 sets out a physical map of plasmid pGBS416ARAABD.

DETAILED DESCRIPTION OF A PREFERRED EMBODIMENT

SEQ ID NO: 1 sets out the wild-type xylose isomerase sequence from *Bacteroides uniformis* ATCC 8492. Genbank accession no. AAYH02000036.

SEQ ID NO: 2 sets out a codon optimized sequence derived from SEQ ID NO: 1.

SEQ ID NO: 3 sets out the amino acid sequence of xylose isomerase from *Bacteroides uniformis* ATCC 8492.

SEQ ID NO: 4 sets out the sequence of plasmid pPWT080.

SEQ ID NO: 5 sets out the sequence of forward primer.

SEQ ID NO: 6 sets out the sequence of reverse primer.

SEQ ID NO: 7 sets out the sequence of the forward multifunctional primer for diagnostic PCR.

SEQ ID NO: 8 sets out the sequence of reverse multifunctional primer for diagnostic PCR.

SEQ ID NO: 9 sets out the sequence of forward primer RKI1-probe.

SEQ ID NO: 10 sets out the sequence of reverse primer RKI1-probe.

SEQ ID NO: 11 sets out the sequence of forward primer kanMX-cassette.

SEQ ID NO: 12 sets out the sequence of reverse primer kanMX-cassette.

SEQ ID NO: 13 sets out the sequence of forward primer.

SEQ ID NO: 14 sets out the sequence of reverse primer.

SEQ ID NO: 15 sets out the sequence of forward multifunctional primer for diagnostic PCR.

SEQ ID NO: 16 sets out the sequence of reverse multifunctional primer for diagnostic PCR.

SEQ ID NO: 17 sets out the sequence of sequence of plasmid pPWT018

SEQ ID NO: 18 sets out the sequence of forward primer integration pPWT018.

SEQ ID NO: 19 sets out the sequence of reverse primer integration pPWT018.

SEQ ID NO: 20 sets out the sequence of forward primer SIT2-probe.

SEQ ID NO: 21 sets out the sequence of reverse primer SIT2-probe.

SEQ ID NO: 22 sets out the sequence of forward primer to amplify araABD expression cassette.

SEQ ID NO: 23 sets out the sequence of reverse primer to amplify araABD expression cassette.

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The various embodiments of the invention described herein may be cross-combined.

The Sugar Composition

The sugar composition according to the invention comprises glucose, arabinose and galactose. In the process of the invention, advantageously the sugars glucose, galactose and arabinose are converted into fermentation product.

Any sugar composition may be used in the invention that suffices those criteria. In a preferred embodiment, the sugar composition is a hydrolysate of one or more lignocellulosic material. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 1. The listed lignocelluloses include: corn cobs, corn fiber, rice hulls, melon shells, sugar beet pulp, wheat straw, sugar cane bagasse, wood, grass and olive pressings.

TABLE 1

Overview of sugar compositions from lignocellulosic materials.

| Lignocellulosic material | Gal | Xyl | Ara | Man | Glu | Rham | Sum | %. Gal. | Lit. |
|---|---|---|---|---|---|---|---|---|---|
| Corn cob a | 10 | 286 | 36 | | 227 | 11 | 570 | 1.7 | (1) |
| Corn cob b | 131 | 228 | 160 | | 144 | | 663 | 19.8 | (1) |
| Rice hulls a | 9 | 122 | 24 | 18 | 234 | 10 | 417 | 2.2 | (1) |
| Rice hulls b | 8 | 120 | 28 | | 209 | 12 | 378 | 2.2 | (1) |
| Melon Shells | 6 | 120 | 11 | | 208 | 16 | 361 | 1.7 | (1) |
| Sugar beet pulp | 51 | 17 | 209 | 11 | 211 | 24 | 523 | 9.8 | (2) |
| Whea straw Idaho | 15 | 249 | 36 | | 396 | | 696 | 2.2 | (3) |
| Corn fiber | 36 | 176 | 113 | | 372 | | 697 | 5.2 | (4) |
| Cane Bagasse | 14 | 180 | 24 | 5 | 391 | | 614 | 2.3 | (5) |
| Corn stover | 19 | 209 | 29 | | 370 | | 626 | | (6) |
| Athel (wood) | 5 | 118 | 7 | 3 | 493 | | 625 | 0.7 | (7) |
| *Eucalyptus* (wood) | 22 | 105 | 8 | 3 | 445 | | 583 | 3.8 | (7) |
| CWR (grass) | 8 | 165 | 33 | | 340 | | 546 | 1.4 | (7) |
| JTW (grass) | 7 | 169 | 28 | | 311 | | 515 | 1.3 | (7) |
| MSW | 4 | 24 | 5 | 20 | 440 | | 493 | 0.9 | (7) |
| Reed Canary Grass Veg | 16 | 117 | 30 | 6 | 209 | 1 | 379 | 4.2 | (8) |
| Reed Canary Grass Seed | 13 | 163 | 28 | 6 | 265 | 1 | 476 | 2.7 | (9) |
| Olive pressing residu | 15 | 111 | 24 | 8 | 329 | | 487 | 3.1 | (9) |
| | | | | | | | Avg | 3.8 | |

Gal = galactose, Xyl = xylose, Ara = arabinose, Man = mannose, Glu = glutamate, Rham = rhamnose. The percentage galactose (% Gal) and literature source is given.

It is clear from table 1 that in these lignocelluloses a considerable amount of sugar (on average 3.8%) is galactose. The conversion of galactose to fermentation product is thus of great economic importance.

The Mixed Sugar Cell

The mixed sugar cell comprising the genes araA, araB and araD as defined hereafter. It is able to ferment glucose, arabinose and galactose. In one embodiment of the invention the mixed sugar cell is able to ferment one or more additional sugar, preferably C5 and/or C6 sugar. In an embodiment of the invention the mixed sugar cell comprises one or more of: a xylA-gene and/or XKS1-gene, to allow the mixed sugar cell to ferment xylose; deletion of the aldose reductase (GRE3) gene; overexpression of PPP-genes TAL1, TKL1, RPE1 and RKI1 to allow the increase of the flux through the pentose phosphate pass-way in the cell.

In one embodiment of the invention the mixed sugar cell is able to ferment one or more additional sugar, preferably C5 and/or C6 sugars. In an embodiment of the invention the mixed sugar cell comprises one or more of: a xylA-gene, XYL1 gene and XYL2 gene and/or XKS1-gene, to allow the mixed sugar cell to ferment xylose; deletion of the aldose reductase (GRE3) gene; overexpression of PPP-genes TAL1, TKL1, RPE1 and RKI1 to allow the increase of the flux through the pentose phosphate pass-way in the cell.

In an embodiment, the mixed sugar cell is an industrial cell, more preferably an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial mixed sugar cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

In an embodiment the mixed sugar cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions.

For phenolics: several tens of milligrams per liter, up to a gram per liter, depending on the feedstock, the pretreatment and the hydrolysis conditions.

The mixed sugar strains according to the invention are inhibitor tolerant, i.e. they can withstand common inhibitors at the level that they typically have with common pretreatment and hydrolysis conditions, so that the mixed sugar strains can find broad application, i.e. it has high applicability for different feedstock, different pretreatment methods and different hydrolysis conditions.

In one embodiment, the industrial mixed sugar cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

In an embodiment, the mixed sugar cell is marker-free. As used herein, the term "marker" refers to a gene encoding a trait or a phenotype which permits the selection of, or the screening for, a host cell containing the marker. Marker-free means that markers are essentially absent in the mixed sugar cell. Being marker-free is particularly advantageous when antibiotic markers have been used in construction of the mixed sugar cell and are removed thereafter. Removal of markers may be done using any suitable prior art technique, e.g intramolecular recombination. A suitable method of marker removal is illustrated in the examples.

A mixed sugar cell may be able to convert plant biomass, celluloses, hemicelluloses, pectins, rhamnose, galactose, frucose, maltose, maltodextrines, ribose, ribulose, or starch, starch derivatives, sucrose, lactose and glycerol, for example into fermentable sugars. Accordingly, a mixed sugar cell may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The mixed sugar cell further may comprise those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the mixed sugar cell a cell that is naturally capable of alcoholic fermentation, preferably, anaerobic alcoholic fermentation. A mixed sugar cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a mixed sugar cell may be naturally present in the cell or may be introduced or modified by genetic modification.

Construction of the Mixed Sugar Strain

The genes may be introduced in the mixed sugar cell by introduction into a host cell:
 a) a cluster consisting of PPP-genes TAL1, TKL1, RPE1 and RKI1, under control of strong promoters,
 b) a cluster consisting of a xylA-gene and the XKS1-gene both under control of constitutive promoters,
 c) a cluster consisting of the genes araA, araB and araD and/or a cluster of xylA-gene and/or the XKS1-gene; and
 d) deletion of an aldose reductase gene
and adaptive evolution to produce the mixed sugar cell. The above cell may be constructed using recombinant expression techniques.

Recombinant Expression

The cell of the invention is a recombinant cell. That is to say, a cell of the invention comprises, or is transformed with or is genetically modified with a nucleotide sequence that does not naturally occur in the cell in question.

Techniques for the recombinant expression of enzymes in a cell, as well as for the additional genetic modifications of a cell of the invention are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Typically, the nucleic acid construct may be a plasmid, for instance a low copy plasmid or a high copy plasmid. The cell according to the present invention may comprise a single or multiple copies of the nucleotide sequence encoding a enzyme, for instance by multiple copies of a nucleotide construct or by use of construct which has multiple copies of the enzyme sequence.

The nucleic acid construct may be maintained episomally and thus comprise a sequence for autonomous replication, such as an autosomal replication sequence sequence. A suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265, 186).

Most episomal or 2μ plasmids are relatively unstable, being lost in approximately $10^{-2}$ or more cells after each generation. Even under conditions of selective growth, only 60% to 95% of the cells retain the episomal plasmid. The copy number of most episomal plasmids ranges from 10-40 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent. Typically, the enzyme encoding sequence will be operably linked to one or more nucleic acid sequences, capable of providing for or aiding the transcription and/or translation of the enzyme sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Promotors are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a cell of the invention, the 3'-end of the nucleotide acid sequence encoding enzyme preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the enzyme comprises a terminator. Preferably, such terminators are combined with mutations that prevent nonsense mediated mRNA decay in the host cell of the invention (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Antibiotic resistance markers may be most convenient for the transformation of polyploid host cells, Also non-antibiotic resistance markers may be used, such as auxotrophic markers (URA3, TRPI, LEU2) or the *S. pombe* TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0 635 574 and are based on the use of bidirectional markers such as the *A. nidulans* amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

The recombination process may thus be executed with known recombination techniques. Various means are known to those skilled in the art for expression and overexpression of enzymes in a cell of the invention. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters.

In an embodiment, the mixed sugar cell is markerfree, which means that no auxotrophic or dominant markers, in particular antibiotic resistance markers, are present in the genome or extra-chromosomally.

The coding sequence used for overexpression of the enzymes mentioned above may preferably be homologous to the host cell of the invention. However, coding sequences that are heterologous to the host cell of the invention may be used.

Overexpression of an enzyme, when referring to the production of the enzyme in a genetically modified cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Preferably in a host cell of the invention, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

Adaptation

Adaptation is the evolutionary process whereby a population becomes better suited (adapted) to its habitat or habitats. This process takes place over several to many generations, and is one of the basic phenomena of biology.

The term adaptation may also refer to a feature which is especially important for an organism's survival. Such adaptations are produced in a variable population by the better suited forms reproducing more successfully, by natural selection.

Changes in environmental conditions alter the outcome of natural selection, affecting the selective benefits of subsequent adaptations that improve an organism's fitness under the new conditions. In the case of an extreme environmental change, the appearance and fixation of beneficial adaptations can be essential for survival. A large number of different factors, such as e.g. nutrient availability, temperature, the availability of oxygen, etcetera, can drive adaptive evolution.

Fitness

There is a clear relationship between adaptedness (the degree to which an organism is able to live and reproduce in a given set of habitats) and fitness. Fitness is an estimate and a predictor of the rate of natural selection. By the application of natural selection, the relative frequencies of alternative phenotypes will vary in time, if they are heritable.

Genetic Changes

When natural selection acts on the genetic variability of the population, genetic changes are the underlying mechanism. By this means, the population adapts genetically to its circumstances. Genetic changes may result in visible structures, or may adjust the physiological activity of the organism in a way that suits the changed habitat.

The Adaptive Evolution

The mixed sugar cells are in their preparation subjected to adaptive evolution. A cell of the invention may be adapted to sugar utilisation by selection of mutants, either spontaneous or induced (e.g. by radiation or chemicals), for growth on the desired sugar, preferably as sole carbon source, and more preferably under anaerobic conditions. Selection of mutants may be performed by techniques including serial transfer of cultures as e.g. described by Kuyper et al. (2004, FEMS Yeast Res. 4: 655-664) or by cultivation under selective pressure in a chemostat culture. E.g. in a preferred host cell of the invention at least one of the genetic modifications described above, including modifications obtained by selection of mutants, confer to the host cell the ability to grow on the xylose as carbon source, preferably as sole carbon source, and preferably under anaerobic conditions. Preferably the cell produce essentially no xylitol, e.g. the xylitol produced is below the detection limit or e.g. less than about 5, about 2, about 1, about 0.5, or about 0.3% of the carbon consumed on a molar basis.

Adaptive evolution is also described e.g. in Wisselink H. W. et al, Applied and Environmental Microbiology August 2007, p. 4881-4891

In one embodiment of adaptive evolution a regimen consisting of repeated batch cultivation with repeated cycles of consecutive growth in different media is applied, e.g. three media with different compositions (glucose, xylose, and arabinose; xylose and arabinose. See Wisselink et al. (2009) Applied and Environmental Microbiology, February 2009, p. 907-914.

Yeast Transformation and Genetic Stability

Genetic engineering, i.e. transformation of yeast cells with recombinant DNA, became feasible for the first time in 1978 [Beggs, 1978; Hinnen et al., 1978]. Recombinant DNA technology in yeast has established itself since then. A multitude of different vector constructs are available. Generally, these plasmid vectors, called shuttle vectors, contain genetic material derived from *E. coli* vectors consisting of an origin of replication and a selectable marker (often the βlactamase gene, ampR), which enable them to be propagated in *E. coli* prior to transformation into yeast cells. Additionally, the shuttle vectors contain a selectable marker for selection in yeast. Markers can be genes encoding enzymes for the synthesis of a particular amino acid or nucleotide, so that cells carrying the corresponding genomic deletion (or mutation) are complemented for auxotrophy or autotrophy. Alternatively, these vectors contain heterologous dominant resistance markers, which provides recombinant yeast cells (i.e. the cells that have taken up the DNA and express the marker gene) resistance towards certain antibiotics, like g418 (Geneticin), hygromycinB or phleomycin. In addition, these vectors may contain a sequence of (combined) restriction sites (multiple cloning site or MCS) which will allow to clone foreign DNA into these sites, although alternative methods exist as well.

Traditionally, four types of shuttle vectors can be distinguished by the absence or presence of additional genetic elements:

Integrative plasmids (YIp) which by homologous recombination are integrated into the host genome at the locus of the marker or another gene, when this is opened by restriction and the linearized DNA is used for transformation of the yeast cells. This generally results in the presence of one copy of the foreign DNA inserted at this particular site in the genome.

Episomal plasmids (YEp) which carry part of the 2μ plasmid DNA sequence necessary for autonomous replication in yeast cells. Multiple copies of the transformed plasmid are propagated in the yeast cell and maintained as episomes.

Autonomously replicating plasmids (YRp) which carry a yeast origin of replication (ARS, autonomously replicated sequence) that allows the transformed plasmids to be propagated several hundred-fold.

CEN plasmids (YCp) which carry in addition to an ARS sequence a centromeric sequence (derived from one of the nuclear chromosomes) which normally guarantees stable mitotic segregation and usually reduces the copy number of self-replicated plasmid to just one.

These plasmids are being introduced into the yeast cells by transformation. Transformation of yeast cells may be achieved by several different techniques, such as permeabilization of cells with lithium acetate (Ito et al, 1983) and electroporation methods.

In commercial application of recombinant microorganisms, plasmid instability is the most important problem. Instability is the tendency of the transformed cells to lose their engineered properties because of changes to, or loss of, plasmids. This issue is discussed in detail by Zhang et al (Plasmid stability in recombinant *Saccharomyces cerevisiae*. Biotechnology Advances, Vol. 14, No. 4, pp. 401-435, 1996). Strains transformed with integrative plasmids are extremely stable, even in the absence of selective pressure (Sherman, F. dbb.urmc.rochester.edu/labs/sherman f/yeast/9.html and references therein).

The heterologous DNA is usually introduced into the organism in the form of extra-chromosomal plasmids (YEp, YCp and YRp). Unfortunately, it has been found with both bacteria and yeasts that the new characteristics may not be retained, especially if the selection pressure is not applied continuously. This is due to the segregational instability of the hybrid plasmid when recombinant cells grow for a long period of time. This leads to population heterogeneity and clonal variability, and eventually to a cell population in which the majority of the cells has lost the properties that were introduced by transformation. If vectors with auxotrophic markers are being used, cultivation in rich media often leads to rapid loss of the vector, since the vector is only retained in minimal media. The alternative, the use of dominant antibiotic resistance markers, is often not compatible with production processes. The use of antibiotics may not be desired from a registration point of view (the possibility that trace amounts of the antibiotic end up in the end product) or for economic reasons (costs of the use of antibiotics at industrial scale).

Loss of vectors leads to problems in large scale production situations. Alternative methods for introduction of DNA do exist for yeasts, such as the use of integrating plasmids (YIp). The DNA is integrated into the host genome by recombination, resulting in high stability. (Caunt, P. Stability of recombinant plasmids in yeast. Journal of Biotechnology 9 (1988) 173-192). We have found that an integration method using the host transposons are a good alternative.

Transposons

In an embodiment of the invention, the cell may comprise more than one copy of desired gene(s). For instance, two or more xylose isomerase gene or xylose reductase gene and xylitol dehydrogenase may be integrated into the mixed sugar cell genome. This may be executed in any way known in the art that leads to introduction of the genes. In a preferred embodiment, this may be accomplished using a vector with parts homologous to repeated sequences (transposons), of the host cell. When the host cell is a yeast cell, suitable repeated sequences are the long terminal repeats (LTR) of the Ty element, known as delta sequence.

Ty elements fall into two rather similar subfamilies called Ty1 and Ty2. These elements are about 6 kilobases (kb) in length and are bounded by long terminal repeats (LTR), sequences of about 335 base pairs (Boeke J D et al, The *Saccharomyces cerevisiae* Genome Contains Functional and Nonfunctional Copies of Transposon Ty1. Molecular and Cellular Biology, April 1988, p. 1432-1442 Vol. 8, No. 4). In the fully sequenced *S. cerevisiae* strain, S288c, the most abundant transposons are Ty1 (31 copies) and Ty2 (13 copies) (Gabriel A, Dapprich J, Kunkel M, Gresham D, Pratt S C, et al. (2006) Global mapping of transposon location. PLoS Genet. 2(12): e212.doi:10.1371/journal.pgen.0020212). These transposons consist of two overlapping open reading frames (ORFs), each of which encode several proteins. The coding regions are flanked by the aforementioned, nearly identical LTRs. Other, but less abundant and more distinct Ty elements in *S. cereviaise* comprise Ty3, Ty4 and Ty5. For each family of full-length Ty elements there are an order of magnitude more solo LTR elements dispersed through the genome. These are thought to arise by LTR-LTR recombination of full-length elements, with looping out of the internal protein encoding regions.

The retrotransposition mechanism of the Ty retrotransposon has been exploited to integrate multiple copies throughout the genome (Boeke et al., 1988; Jacobs et al., 1988). The long terminal repeats (LTR) of the Ty element, known as delta sequences, are also good targets for integration by homologous recombination as they exist in about 150-200 copies that are either Ty associated or solo sites (Boeke, 1989; Kingsman and Kingsman, 1988). (Parekh R. N. (1996). An Integrating Vector for Tunable, High Copy, Stable Integration into the Dispersed Ty DELTA Sites of *Saccharomyces cerevisiae*. Biotechnol. Prog. 1996, 12, 16-21).

The Host Cell

The host cell may be any host cell suitable for production of a useful product. A cell of the invention may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a cell of the invention may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic or oxygen limited fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the suitable for use as a cell of the present invention are morphologically, physiologically, and genetically distinct from yeasts. Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell of the invention may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

In one embodiment the host cell may be yeast.

Preferably the host is an industrial host, more preferably an industrial yeast. An industrial host and industrial yeast cell may be defined as follows. The living environments of yeast cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. Examples of industrial yeast (*S. cerevisiae*) are Ethanol Red® (Fermentis), Fermiol® (DSM) and Thermosacc® (Lallemand).

In an embodiment the host is inhibitor tolerant. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

Preferably the host cell is industrial and inhibitor tolerant.

AraA, AraB and AraD Genes

A cell of the invention is capable of using arabinose. A cell of the invention is therefore, be capable of converting L-arabinose into L-ribulose and/or xylulose 5-phosphate and/or into a desired fermentation product, for example one of those mentioned herein.

Organisms, for example S. cerevisiae strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a cell of the invention is order that it is capable of using arabinose. Such an approach is given is described in WO2003/095627. araA, araB and araD genes from *Lactobacillus plantanum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591.

PPP-Genes

A cell of the invention may comprise one or more genetic modifications that increases the flux of the pentose phosphate pathway. In particular, the genetic modification(s) may lead to an increased flux through the non-oxidative part pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s = \mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RKI1.

The enzyme "transketolase" (EC 2.2.1.1) is herein defined as an enzyme that catalyses the reaction: D-ribose 5-phosphate+D-xylulose 5-phosphate<->sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<->D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate: D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Xylose Isomerase or Xylose Reductase and Xylitol Dehydrogenase Genes

According to the invention, one, two or more copies of one or more xylose isomerase gene and/or one or more xylose reductase and xylitol dehydrogenase are introduced into the genome of the host cell. The presence of these two or more genetic elements confers on the cell the ability to convert xylose by isomerisation or reduction.

In one embodiment, the one, two or more copies of one or more xylose isomerase gene are introduced into the genome of the host cell.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, such a mixed sugar cell is capable of isomerising xylose to xylulose. The ability of isomerising xylose to xylulose is conferred on the host cell by transformation of the host cell with a nucleic acid construct comprising a nucleotide sequence encoding a defined xylose isomerase. A mixed sugar cell isomerises xylose into xylulose by the direct isomerisation of xylose to xylulose.

A unit (U) of xylose isomerase activity may herein be defined as the amount of enzyme producing 1 nmol of xylulose per minute, under conditions as described by Kuyper et al. (2003, FEMS Yeast Res. 4: 69-78). The Xylose isomerise gene may have various origin, such as for example *Pyromyces* sp. as disclosed in WO2006/009434. Other suitable origins are *Bacteroides*, in particular *Bacteroides uniformis* as described in PCT/EP2009/52623, *Bacillus*, in particular *Bacillus stearothermophilus* as described in PCT/EP2009/052625.

In another embodiment, the two or more copies of one or more xylose reductase and xylitol dehydrogenase genes are introduced into the genome of the host cell. In this embodiment the conversion of xylose is conducted in a two step conversion of xylose into xylulose via a xylitol intermediate as catalysed by xylose reductase and xylitol dehydrogenase, respectively. In an embodiment thereof xylose reductase (XR), xylitol dehydrogenase (XDH), and xylokinase (XK) may be overexpressed, and optionally one or more of genes encoding NADPH producing enzymes are up-regulated and one or more of the genes encoding NADH consuming enzymes are up-regulated, as disclosed in WO 2004085627.

XKS1 Gene

A cell of the invention may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell of the invention is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP: D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a cell of the invention, a genetic modification or modifications that increase(s) the specific xylulose kinase activity may be combined with any of the modifications increasing the flux of the pentose phosphate pathway as described above. This is not, however, essential.

Thus, a host cell of the invention may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s)

causing the overexpression. It is to be understood that these levels of overexpression may apply to the steady state level of the enzyme's activity, the steady state level of the enzyme's protein as well as to the steady state level of the transcript coding for the enzyme.

Aldose Reductase (GRE3) Gene Deletion

In the embodiment, where XI is used as gene to convert xylose, it may be advantageoud to reduce aldose reductase activity. A cell of the invention may therefore comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell (herein called GRE3 deletion). Host cells may comprise multiple copies of genes encoding unspecific aldose reductases as a result of di-, poly- or aneu-ploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell of the invention is a nucleotide sequence encoding a polypeptide with aldose reductase activity.

Thus, a host cell of the invention comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

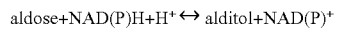

The enzyme has a wide specificity and is also known as aldose reductase; polyol dehydrogenase (NADP⁺); alditol: NADP oxidoreductase; alditol:NADP⁺ 1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

Sequence Identity

Sequence identity (or sequence similarity) is herein defined as a relationship between two or more amino acid (polypeptide or protein) sequences or two or more nucleic acid (polynucleotide) sequences, as determined by comparing the sequences. Usually, sequence identities or similarities are compared, typically over the whole length of the sequences compared. However, sequences may be compared over shorter comparison windows. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. Preferred parameters for nucleic acid sequences comparison using BLASTP are gap open 11.0, gap extend 1, DNA full matrix (DNA identity matrix).

Optionally, in determining the degree of amino acid similarity, the skilled person may also take into account so-called "conservative" amino acid substitutions, as will be clear to the skilled person.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine.

Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; He to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution.

These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

To increase the likelihood that the introduced enzyme is expressed in active form in a cell of the invention, the corresponding encoding nucleotide sequence may be adapted to optimise its codon usage to that of the chosen yeast cell. Several methods for codon optimisation are known in the art. A preferred method to optimise codon usage of the nucleotide sequences to that of the yeast is a codon pair optimization technology as disclosed in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

As a simple measure for gene expression and translation efficiency, herein, the Codon Adaptation Index (CAI), as described in Xuhua Xia, Evolutionary Bioinformatics 2007: 3 53-58, is used. The index uses a reference set of highly expressed genes from a species to assess the relative merits of each codon, and a score for a gene is calculated from the frequency of use of all codons in that gene. The index assesses the extent to which selection has been effective in moulding the pattern of codon usage. In that respect it is useful for predicting the level of expression of a gene, for assessing the adaptation of viral genes to their hosts, and for making comparisons of codon usage in different organisms. The index may also give an approximate indication of the likely success of heterologous gene expression. In the codon pair optimized genes according to the invention, the CAI is 0.6 or more, 0.7 or more, 0.8 or more, 0.85 or more, 0.87 or more 0.90 or more, 0.95 or more, or about 1.0.

A cell of the invention is thus a cell that comprises, i.e. has been transformed with, a nucleic acid construct comprising the nucleotide sequence encoding the araA, araB and araD genes as defined above. The nucleic acid construct comprising araA coding sequence preferably is capable of expression of the araA genes in the host cell.

Preferably, the genes are expressed in the cytosol. Cytosolic expression may be achieved by deletion or modification of a mitochondrial or peroxisomal targeting signal.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K. fragilis*.

A cell of the invention may be able to convert plant biomass, celluloses, hemicelluloses, pectins, rhamnose, galactose, frucose, maltose, maltodextrines, ribose, ribulose, or starch, starch derivatives, sucrose, lactose and glycerol, for example into fermentable sugars. Accordingly, a cell of the invention may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The cell further preferably comprises those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

A preferred cell of the invention is a cell that is naturally capable of alcoholic fermentation, preferably, anaerobic alcoholic fermentation. A cell of the invention preferably has a high tolerance to ethanol, a high tolerance to low pH (i.e. capable of growth at a pH lower than about 5, about 4, about 3, or about 2.5) and towards organic acids like lactic acid, acetic acid or formic acid and/or sugar degradation products such as furfural and hydroxy-methylfurfural and/or a high tolerance to elevated temperatures.

Any of the above characteristics or activities of a cell of the invention may be naturally present in the cell or may be introduced or modified by genetic modification.

A cell of the invention may be a cell suitable for the production of ethanol. A cell of the invention may, however, be suitable for the production of fermentation products other than ethanol. Such non-ethanolic fermentation products include in principle any bulk or fine chemical that is producible by a eukaryotic microorganism such as a yeast or a filamentous fungus.

Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred cell of the invention for production of non-ethanolic fermentation products is a host cell that contains a genetic modification that results in decreased alcohol dehydrogenase activity.

In a further aspect the invention relates to fermentation processes in which the cells of the invention are used for the fermentation of a carbon source comprising a source of xylose, such as xylose. In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g. lignocellulose, xylans, cellulose, starch and the like. For release of xylose or glucose units from such carbohydrates, appropriate carbohyrases (such as xylanases, glucanases, amylases and the like) may be added to the fermentation medium or may be produced by the cell. In the latter case the cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art. The fermentation process is a process for the production of a fermentation product such as e.g. ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic, such as Penicillin G or Penicillin V and fermentative derivatives thereof, and a cephalosporin.

Lignocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Pretreatment may be desirable to release sugars that may be fermented according to the invention from the lignocellulosic (including hemicellulosic) material. This steps may be executed with conventional methods, e.g.

Enzymatic Hydrolysis

Enzymatic hydrolysis may be executed with conventional methods.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.,

The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity.

The fermentation process according to the present invention may be run under aerobic and anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention comprises recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 g1/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical mamimum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:
 a. degrading lignocellulose using a method as described herein; and
 b. fermenting the resulting material,
thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermenation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following examples illustrate the invention:

EXAMPLES

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Transformation of S. cerevisiae

Transformation of S. cerevisiae was done as described by Gietz and Woods (2002; Transformation of the yeast by the LiAc/SS carrier DNA/PEG method. Methods in Enzymology 350: 87-96).

Colony PCR

A single colony isolate was picked with a plastic toothpick and resuspended in 50 µl milliQ water. The sample was incubated for 10 minutes at 99° C. 5 µl of the incubated sample was used as a template for the PCR reaction, using Phusion® DNA polymerase (Finnzymes) according to the instructions provided by the supplier.

PCR reaction conditions:

| step 1 | 3' 98° C. | |
| step 2 | 10" 98° C. | |
| step 3 | 15" 58° C. | repeat step 2 to 4 for 30 cycles |
| step 4 | 30" 72° C. | |
| step 5 | 4' 72° C. | |
| step 6 | 30" 20° C. | |

Medium Composition

Growth experiments: Saccharomyces cerevisiae strains are grown on medium having the following composition: 0.67% (w/v) yeast nitrogen base or synthetic medium (Verduyn et al., Yeast 8:501-517, 1992) and either glucose, arabinose, galactose or xylose, or a combination of these substrates (see below). For agar plates the medium is supplemented with 2% (w/v) bacteriological agar.

Ethanol production: cultivations were performed at 30° C. in 100 ml synthetic model medium (Verduyn-medium (Verduyn et al., Yeast 8:501-517, 1992) with 5% glucose, 5% xylose, 3.5% arabinose and 1-1.5% galactose) in the BAM (Biological Activity Monitor, Halotec, The Netherlands). The pH of the medium was adjusted to 4.2 with 2 M NaOH/H2SO4 prior to sterilisation. The synthetic medium for anaerobic cultivation was supplemented with 0.01 g I-1 ergosterol and 0.42 g I-1 Tween 80 dissolved in ethanol (Andreasen and Stier. J. Cell Physiol. 41:23-36, 1953; and Andreasen and Stier. J. Cell Physiol. 43:271-281, 1954). Cultures were stirred by magnetic stirrer. Anaerobic conditions developed rapidly during fermentation as the culture was not aerated. CO2 production was monitored constantly. Sugar conversion and product formation was analyzed by NMR. Growth was monitored by following optical density of the culture at 600 nm on a LKB Ultrospec K spectrophotometer.

Pre-cultures were prepared by inoculating 25 ml Verduyn-medium (Verduyn et al., Yeast 8:501-517, 1992) supplemented with 2% glucose in a 100-ml shake flask with a frozen stock culture or a single colony from agar plate. After incubation at 30° C. in an orbital shaker (200 rpm) for approximately 24 hours, this culture was harvested and used for inoculation of the BAM at an OD 600 of approximately 2.

Example 1

Figure 1:
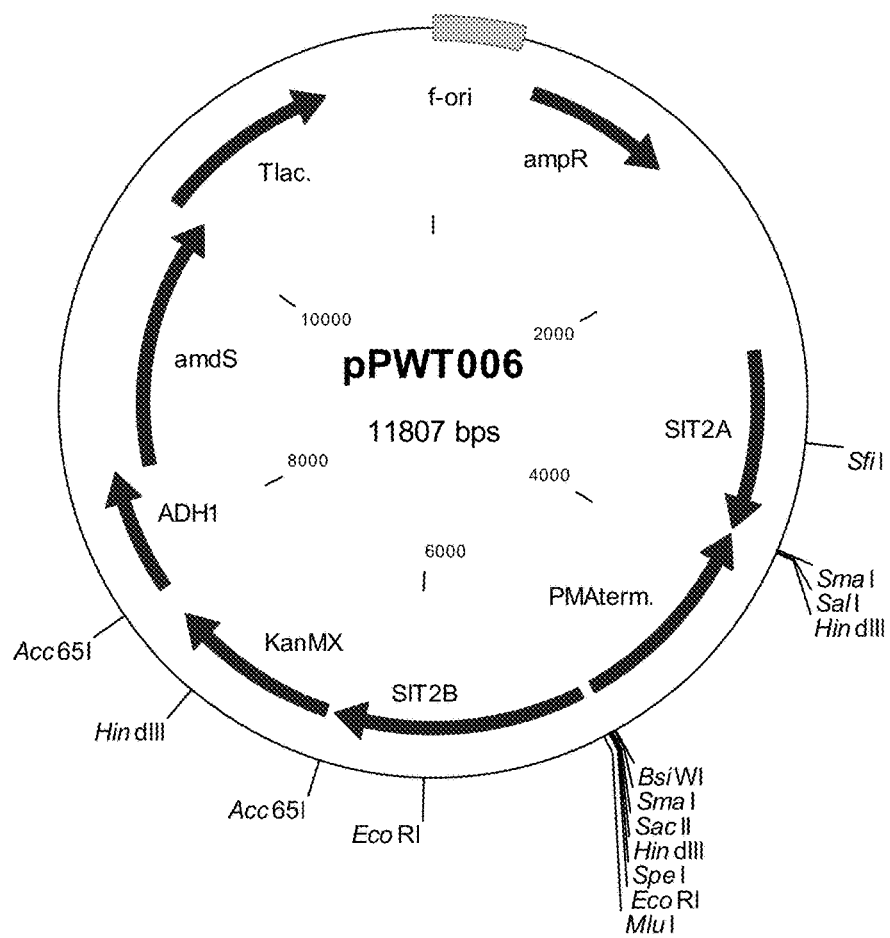
FIG. 1 sets out a physical map of plasmid pPWT006.
Figure 2:
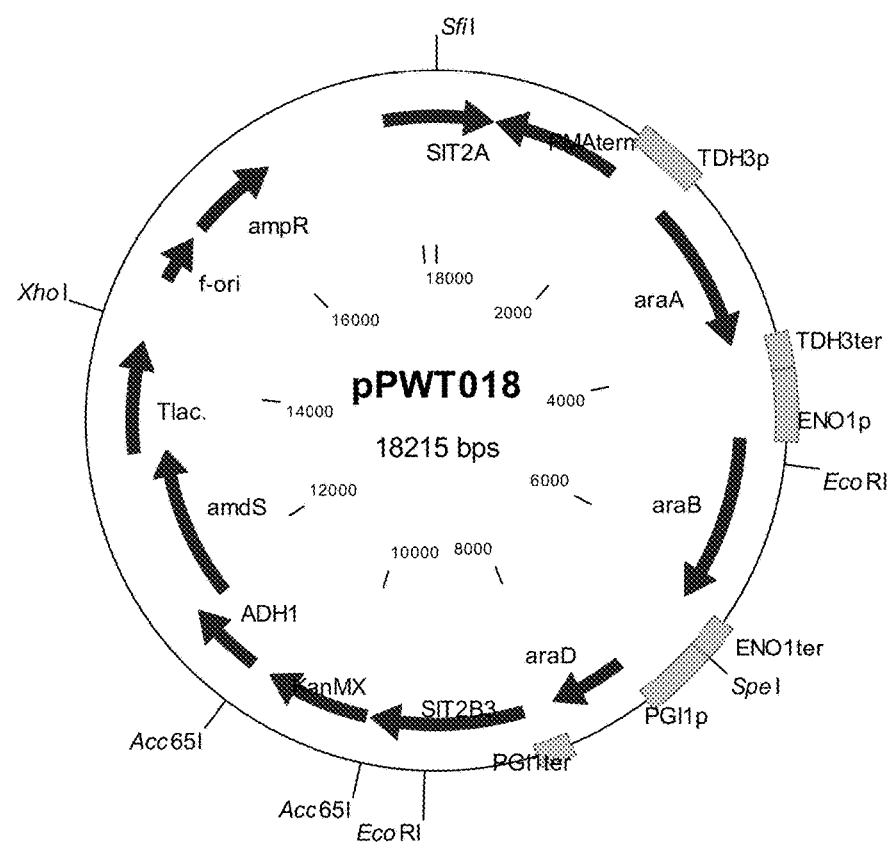
FIG. 2 sets out a physical map of plasmid pPWT018.

Introduction of the Genes araA, araB and araD into the Genome of S. cerevisiae 1.1 Construction of an Expression Vector Containing the Genes for Arabinose Pathway Plasmid pPWT018, as set out in FIG. 2, was constructed as follows: vector pPWT006 (FIG. 1, consisting of a SIT2-locus (Gottlin-Ninfa and Kaback (1986) Molecular and Cell Biology vol. 6, no. 6, 2185-2197) and the markers allowing for selection of transformants on the antibiotic G418 and the ability to grow on acetamide (vide supra), was digested with the restriction enzymes BsiWI and MluI. The kanMX-marker, conferring resistance to G418, was isolated from p427TEF (Dualsystems Biotech) and a fragment containing the amdS-marker has been described in the literature (Swinkels, B. W., Noordermeer, A. C. M. and Renniers, A. C. H. M (1995) The use of the amdS cDNA of Aspergillus nidulans as a dominant, bidirectional selectable marker for yeast transformation. Yeast Volume 11, Issue 1995A, page S579; and U.S. Pat. No. 6,051,431). The genes encoding arabinose isomerase (araA), L-ribulokinase (araB) and L-ribulose-5-phosphate-4-epimerase (araD) from *Lactobacillus plantarum*, as disclosed in patent application WO2008/041840, were synthesized by BaseClear (Leiden, The Netherlands). One large fragment was synthesized, harbouring the three arabinose-genes mentioned above, under control of (or operable linked to) strong promoters from S. cerevisiae, i.e. the TDH3-promoter controlling the expression of the araA-gene, the ENO1-promoter controlling the araB-gene and the PGI1-promoter controlling the araD-gene. This fragment was surrounded by the unique restriction enzymes Acc65I and MluI. Cloning of this fragment into pPWT006 digested with MluI and BsiWI, resulted in plasmid pPWT018 (FIG. 2). The sequence of plasmid pPWT018 is set out in SEQ ID 17.

1.2 Yeast Transformation

CEN.PK113-7D (MATa URA3 HIS3 LEU2 TRP1 MAL2-8 SUC2) was transformed with plasmid pPWT018, which was previously linearized with SfiI (New England Biolabs), according to the instructions of the supplier. A synthetic SfiI-site was designed in the 5'-flank of the SIT2-gene (see FIG. 2). Transformation mixtures were plated on YPD-agar (per liter: 10 grams of yeast extract, 20 grams per liter peptone, 20 grams per liter dextrose, 20 grams of agar) containing 100 µg G418 (Sigma Aldrich) per ml. After two to four days, colonies appeared on the plates, whereas the negative control (i.e. no addition of DNA in the transformation experiment) resulted in blank YPD/G418-plates. The integration of plasmid pPWT018 is directed to the SIT2-locus. Transformants were characterized using PCR and Southern blotting techniques.

Figure 4:
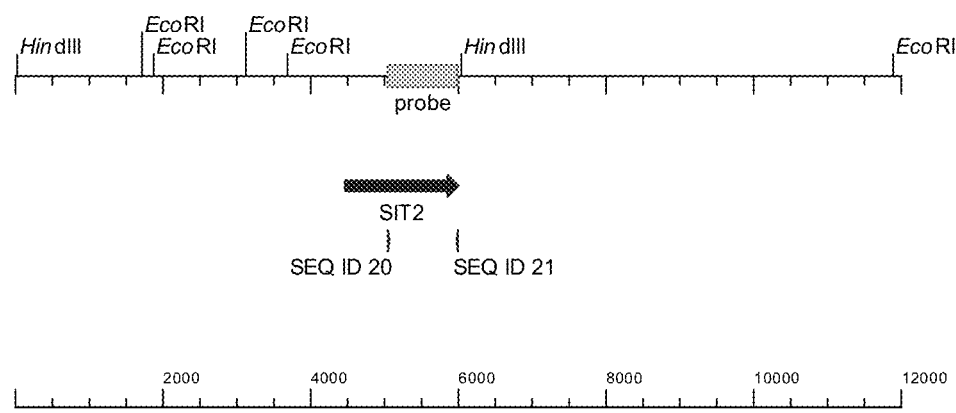
FIG. 4 sets out physical maps of the wild-type SIT2-locus (panel a) and after introduction of the ara-genes by integration of plasmid pPWT018, followed by intramolecular recombination leading to the loss of vector and selectable marker sequences (panel b). The hybridization of the probe is indicated.
Figure 4:
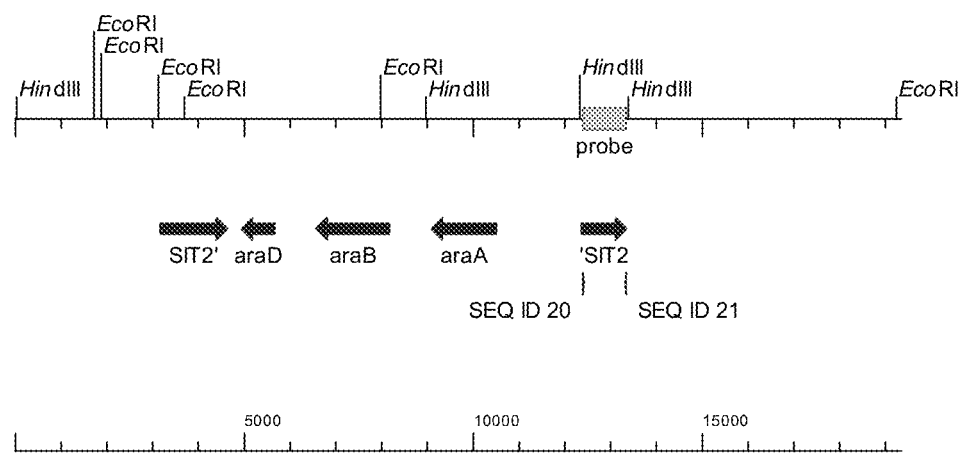

PCR reactions, which are indicative for the correct integration of one copy of plasmid pPWT018, were performed with the primers indicated by SEQ ID 18 and 15, and 15 and 14 (see FIG. 4). With the primer pairs of SEQ ID 18 and 15, the correct integration at the SIT2-locus was checked. If plasmid pPWT018 was integrated in multiple copies (head-to-tail integration), the primer pair of SEQ ID 15 and 14 will give a PCR-product. If the latter PCR product is absent, this is indicative for one copy integration of pPWT018. A strain in which one copy of plasmid pPWT018 was integrated in the SIT2-locus was designated BIE104R2.

1.3 Marker Rescue

In order to be able to transform the yeast strain with other constructs, using the same selection markers, it is necessary to remove the selectable markers. The design of plasmid pPWT018 was such, that upon integration of pPWT018 in the chromosome, homologous sequences are in close proximity of each other. This design allows the selectable markers to be lost by spontaneous intramolecular recombination of these homologous regions.

Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strain BIE104R2 was cultured in YPD-medium (per liter: 10 grams of yeast extract, 20 grams per liter peptone, 20 grams per liter dextrose), starting from a single colony isolate. 25 µl of an overnight culture was used to inoculate fresh YPD medium. After at least five of such serial transfers, the optical density of the culture was determined and cells were diluted to a concentration of approximately 5000 per ml. 100 µl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Cells identical to cells of strain BIE104R2, i.e. without intracellular recombination, still contain the amdS-gene. To those cells, fluoro-acetamide is toxic. These cells will not be able to grow and will not form colonies on a medium containing fluoro-acetamide. However, if intramolecular recombination has occurred, BIE104R2-variants that have lost the selectable markers will be able to grow on the fluoro-acetamide medium, since they are unable to convert fluoro-acetamide into growth inhibiting compounds. Those cells will form colonies on this agar medium.

The thus obtained fluoro-acetamide resistant colonies were subjected to PCR analysis using primers of SEQ ID 18 and 15, and 14 and 19. Primers of SEQ ID 18 and 5 will give a band if recombination of the selectable markers has taken place as intended. As a result, the cassette with the genes araA, araB and araD under control of the strong yeast promoters have been integrated in the SIT2-locus of the genome of the host strain. In that case, a PCR reaction using primers of SEQ ID 14 and 19 should not result in a PCR product, since primer 14 primes in a region that should be lost due to recombination. If a band is obtained with the latter primers, this is indicative for the presence of the complete plasmid pPWT018 in the genome, so no recombination has taken place.

If primers of SEQ ID 18 and 15 do not result in a PCR product, recombination has taken place, but in such a way that the complete plasmid pPWT018 has recombined out of the genome. Not only were the selectable markers lost, but also the arabinose-genes. In fact, wild-type yeast has been retrieved.

Figure 3:
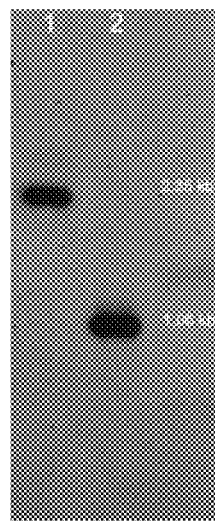
FIG. 3 sets out a Southern blot autoradiogram. Chromosomal DNA of wild-type strain CEN.PK113-7D (lane 1) and BIE104A2 (lane 2) was digested with both EcoRI and HindIII. The blot was hybridized with a specific SIT2-probe.

Isolates that showed PCR results in accordance with one copy integration of pPWT018 were subjected to Southern blot analysis. The chromosomal DNA of strains CEN.PK113-7D and the correct recombinants were digested with EcoRI and HindIII (double digestion). A SIT2-probe was prepared with primers of SEQ ID 20 and 21, using chromosomal DNA of CEN.PK113-7D as a template. The result of the hybridisation experiment is shown in FIG. 3. The expected hybridisation pattern may be deduced from the physical maps as set out in FIG. 4 (panels a and b).

In the wild-type strain, a band of 2.35 kb is observed, which is in accordance with the expected size of the wild type gene (FIG. 4, panel a). Upon integration and partial loss by recombination of the plasmid pPWT018, a band of 1.06 kb was expected (FIG. 4, panel b). Indeed, this band is observed, as shown in FIG. 3 (lane 2).

One of the strains that showed the correct pattern of bands on the Southern blot (as can be deduced from FIG. 3) is the strain designated as BIE104A2.

1.4 Introduction of Four Constitutively Expressed Genes of the Non-Oxidative Pentose Phosphate Pathway

Figure 5:
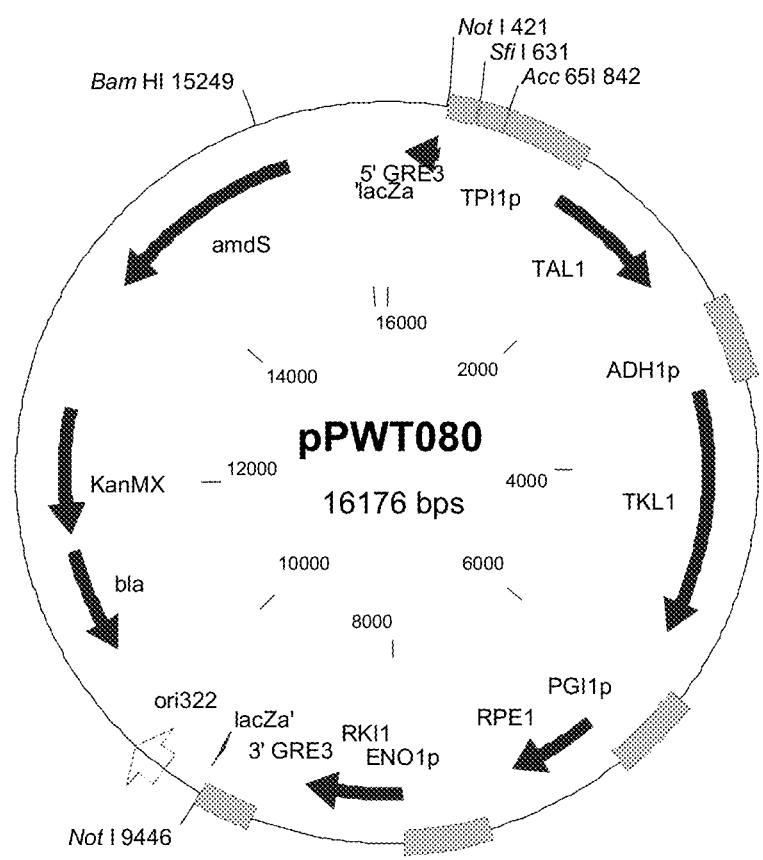
FIG. 5 sets out a physical map of plasmid pPWT080, the sequence of which is given in SEQ ID no. 4.
Figure 6:
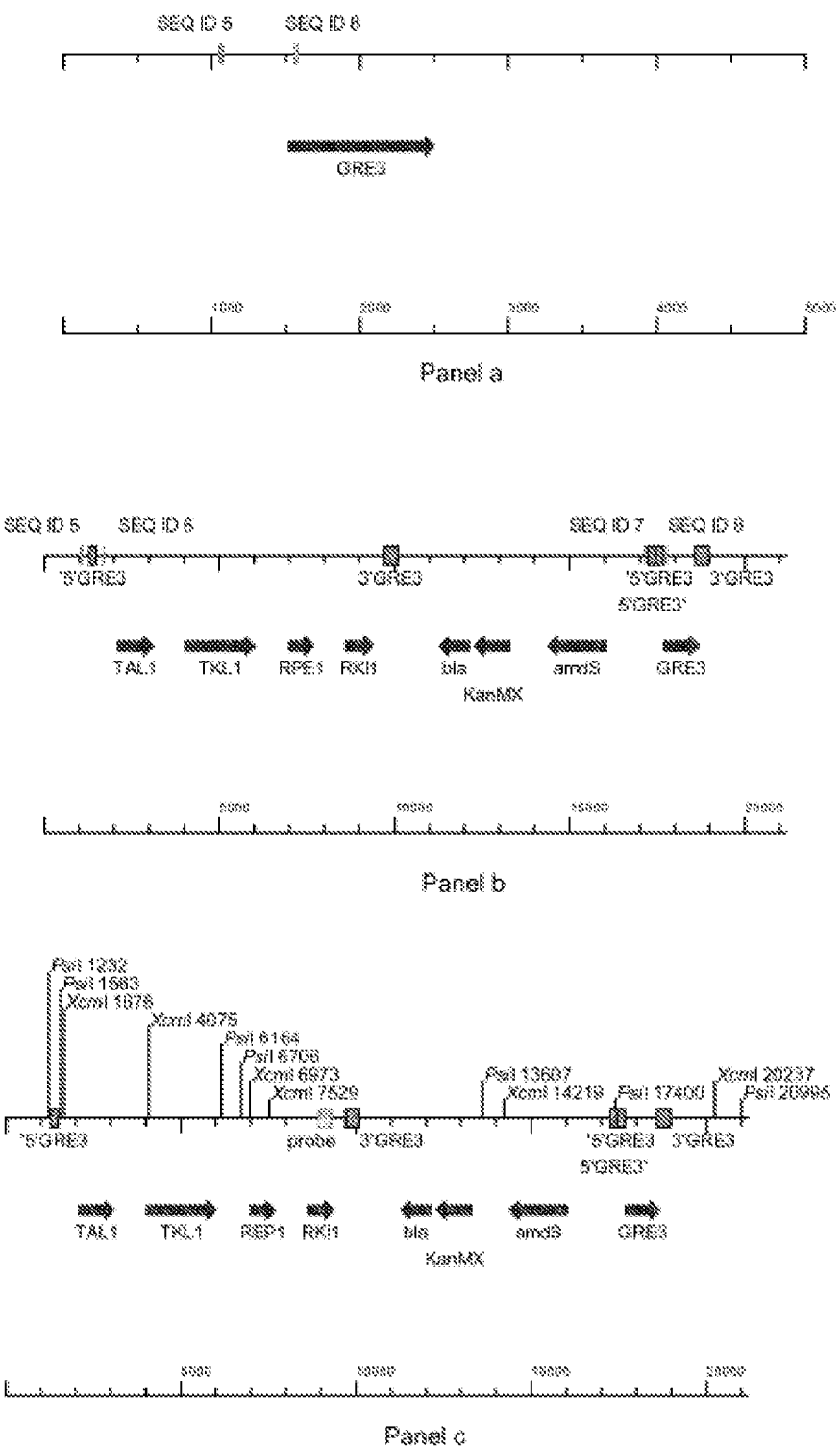
FIG. 6 sets out a physical map of the wild-type GRE3-locus (panel a) and a one copy integration of PWT080 in the GRE3-locus (panel b, showing where the primers bind and panel c, showing where the RKI1-probe binds).
Figure 7:
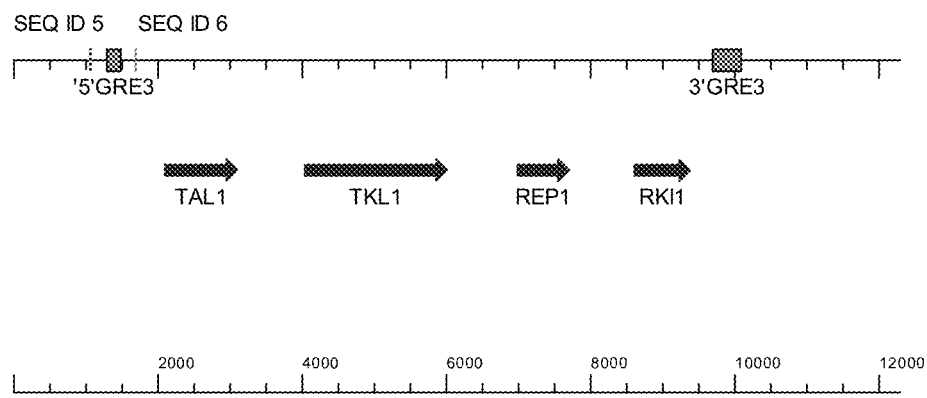
FIG. 7 sets out a physical map of the GRE3-locus, where the coding region of the GRE3-gene was replaced by the integration of the PPP-genes TAL1, TKL1, RKI1 and RPE1. Panel a shows the where the primers of SEQ ID 5 and 6 bind, panel b shows where the RKI1-probe binds.
Figure 7:
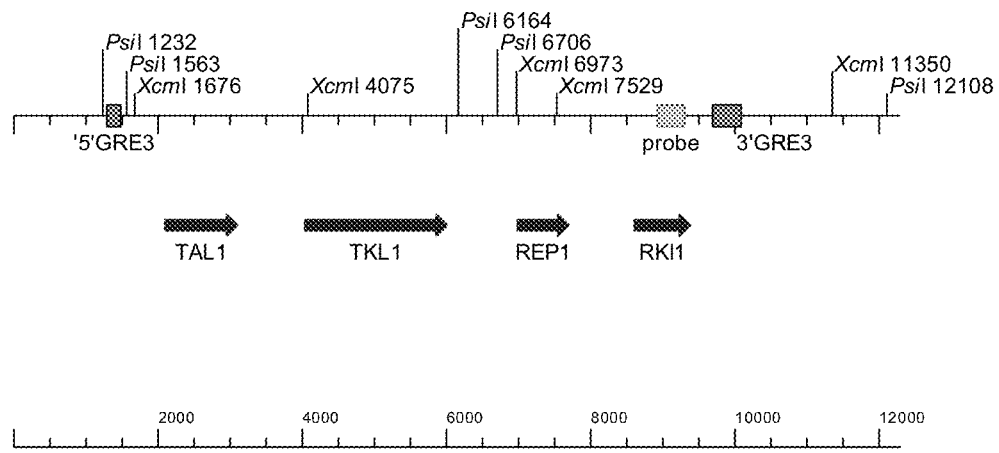

*Saccharomyces cerevisiae* BIE104A2, expressing the genes araA, araB and araD constitutively, was transformed with plasmid pPWT080 (FIG. 5). The sequence of plasmid pPWT080 is set out in SEQ ID NO: 4. The procedure for transformation and selection, after selecting a one copy transformant, are the same as described above in sections 1.1, 1.2 and 1.3). In short, BIE104A2 was transformed with SfiI-digested pPWT080. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

The integration of plasmid pPWT080 is directed to the GRE3-locus. Transformants were characterized using PCR and Southern blotting techniques.

A transformant showing correct integration of one copy of plasmid pPWT080, in accordance with the expected hybridisation pattern, was designated BIE104A2F1.

In order to be able to introduce the genes encoding xylose isomerase and xylulokinase (example 5), it is necessary to remove the selection markers introduced by the integration of plasmid pPWT080. To this end, strain BIE104A2F1 was cultured in YPD-medium, starting from a colony isolate. 25 μl of an overnight culture was used to inoculate fresh YPD-medium. After five serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Fluoro-acetamide resistant colonies were subjected to PCR analysis and, in case of correct PCR-profiles, Southern blot analysis (section 1.3 of example 1). One of the strains that showed the correct pattern of bands on the Southern blot is the strain designated as BIE104A2P1.

Example 2

Adaptive Evolution 2.1 Adaptive Evolution (Aerobically)

Figure 8:
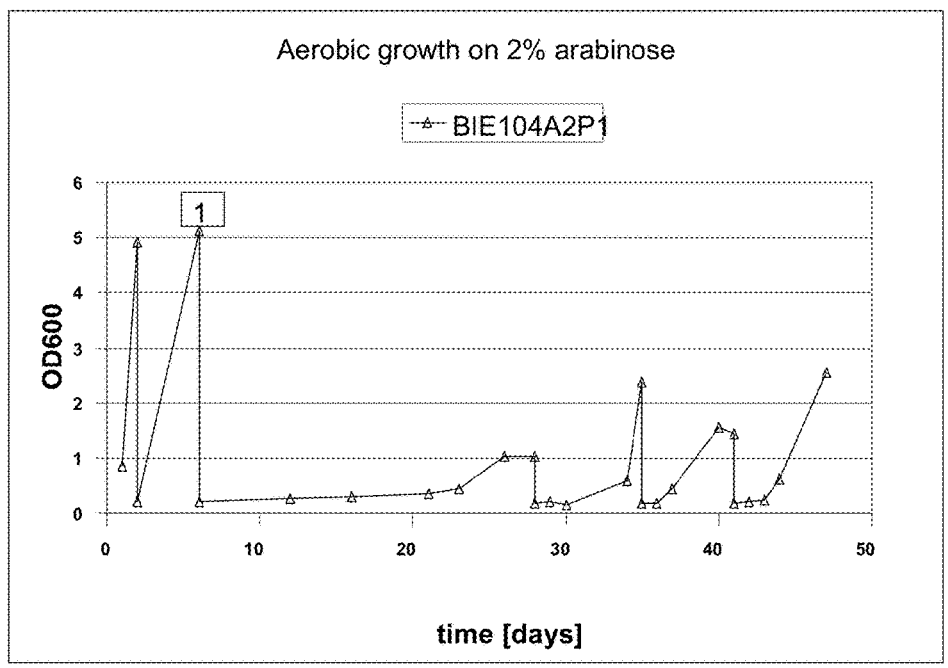
FIG. 8 sets out a growth curves under aerobic conditions of BIE104P1A2 on different media. Strain BIE104A2P1 was pregrown on YNB 2% galactose. Growth curve was started on 2% galactose and 1% arabinose, followed by event indicated in the graph by number (1) transfer to YNB with 2% arabinose as sole carbon source. After reaching an OD 600 more than 1, the culture was transferred to fresh medium with a starting OD 600 of 0.2. Upon three transfers on pure arabinose medium the resulting strain was designated BIE104P1A2c.

Single colony isolate of strain BIE104A2P1 was used to inoculate YNB-medium (Difco) supplemented with 2% galactose. The preculture was incubated for approximately 24 hours at 30° C. and 280 rpm. Cells were harvested and inoculated in YNB medium containing 1% galactose and 1% arabinose at a starting OD600 of 0.2 (FIG. 8). Cells were grown at 30° C. and 280 rpm. The optical density at 600 nm was monitored regularly.

When the optical density reached a value of 5, an aliquot of the culture was transferred to fresh YNB medium containing the same medium. The amount of cells added was such that the starting OD600 of the culture was 0.2. After reaching an OD 600 of 5 again, an aliquot of the culture was transferred to YNB medium containing 2% arabinose as sole carbon source (event indicated by (1) in FIG. 8).

Upon transfer to YNB with 2% arabinose as sole carbon source growth could be observed after approximately two weeks. When the optical density at 600 nm reached a value at least of 1, cells were transferred to a shake flask with fresh YNB-medium supplemented with 2% arabinose at a starting OD600 of 0.2 (FIG. 8).

Sequential transfer was repeated three times, as is set it in FIG. 8. The resulting strain which was able to grow fast on arabinose was designated BIE104A2P1c.

2.2 Adaptive Evolution (Anaerobically)

Figure 9:
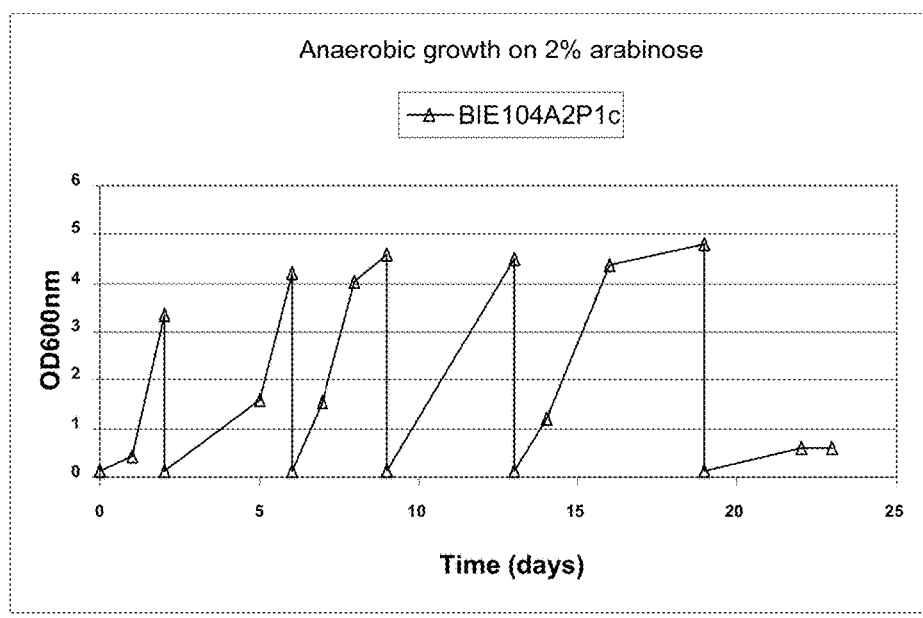
FIG. 9 sets out a growth curves under anaerobic conditions of BIE104P1A2c on YNB 2% arabinose as sole carbon source. After reaching an OD 600 higher than 1, the culture was transferred to fresh medium with a starting OD 600 of 0.2. After several transfers the resulting strain was named BIE104P1A2d (=BIE201).

After adaptation on growth on arabinose under aerobic conditions, a single colony from strain BIE104A2P1c was inoculated in YNB medium supplemented with 2% glucose. The preculture was incubated for approximately 24 hours at 30° C. and 280 rpm. Cells were harvested and inoculated in YNB medium containing 2% arabinose, with optical density $OD^{600}$ of 0.2. The flasks were closed with waterlocks, ensuring anaerobic growth conditions after the oxygen was exhausted from the medium and head space. After reaching an OD 600 minimum of 3, an aliquot of the culture was transferred to fresh YNB medium containing 2% arabinose (FIG. 9), each with optical density $OD^{600}$ of 0.2.

After several transfers the resulting strain was designated BIE104A2P1d (=BIE201).

Example 3

Fermentative Capacity Determination

Figure 10:
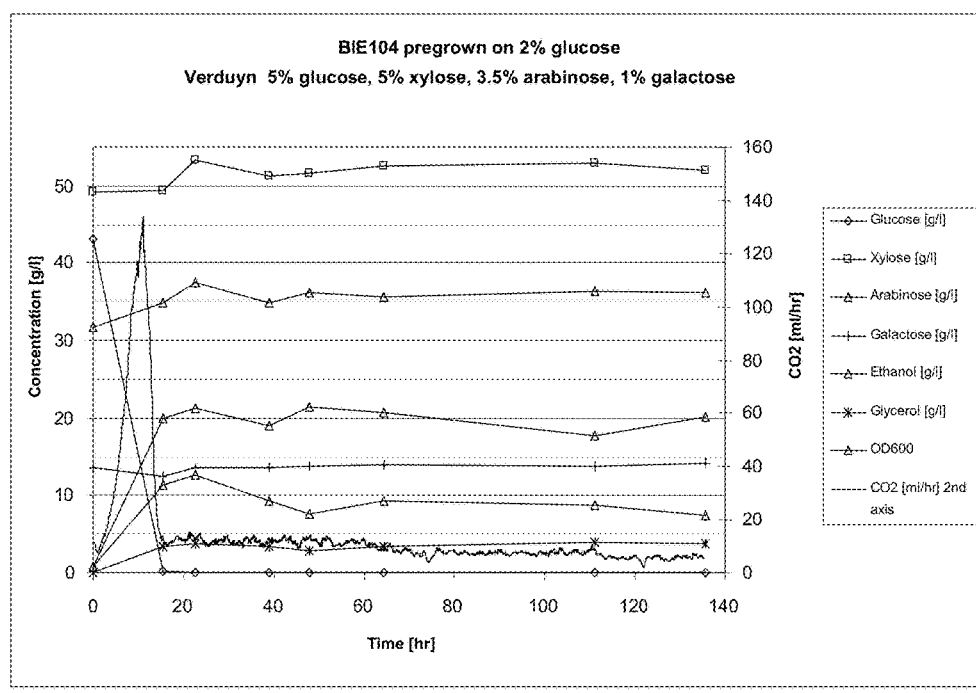
FIG. 10 sets out sugar conversion and product formation of BIE104 on synthetic corn fiber model medium. CO2 production was measured constantly. Growth was monitored by following optical density of the culture. Preculture was grown on 2% glucose.

Single colony isolates of strain BIE104, BIE104A2P1c and BIE201 were used to inoculate YNB-medium (Difco) supplemented with 2% glucose. The precultures were incubated for approximately 24 hours at 30° C. and 280 rpm. Cells were harvested and inoculated in a synthetic model medium (Verduyn et al., Yeast 8:501-517, 1992; 5% glucose, 5% xylose, 3.5% arabinose, 1% galactose) at an initial OD600 of approximately 2 in the BAM. CO2 production was monitored constantly. Sugar conversion and product formation was analyzed by NMR. The data represent the residual amount of sugars at the indicated (glucose, arabinose, galactose and xylose in grams per liter) and the formation of (by-)products (ethanol, glycerol). Growth was monitored by following optical density of the culture at 600 nm (FIG. 10, 11, 12). The experiment was running for approximately 140 hours.

Figure 11:
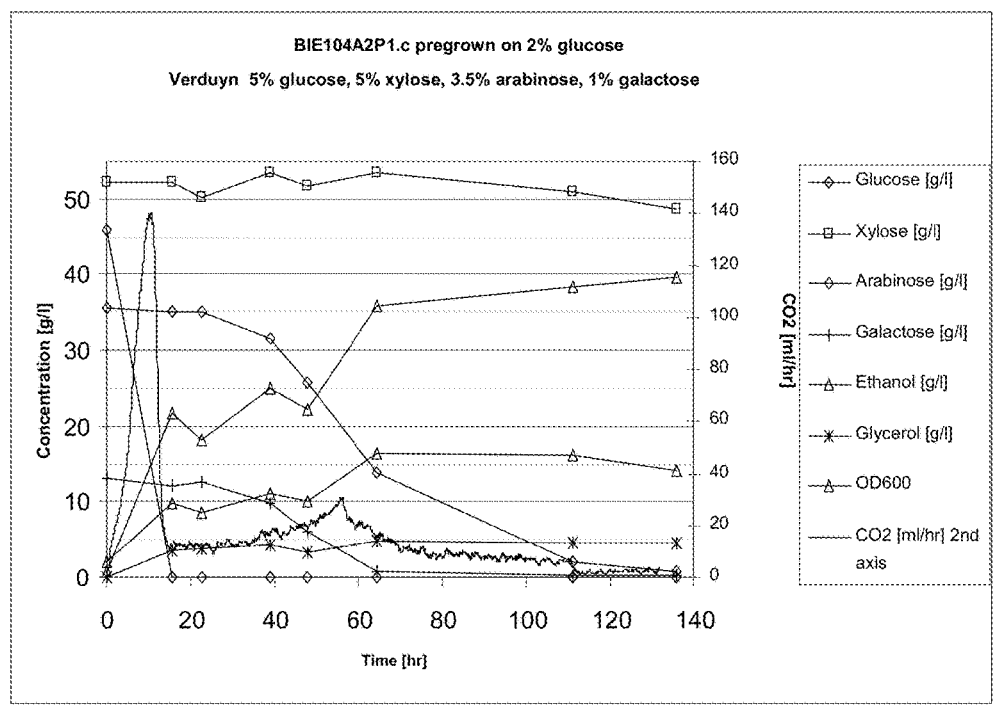
FIG. 11 sets out sugar conversion and product formation of BIE104P1A2c on synthetic corn fiber model medium. CO2 production was measured constantly. Growth was monitored by following optical density of the culture. Preculture was grown on 2% glucose.
Figure 12:
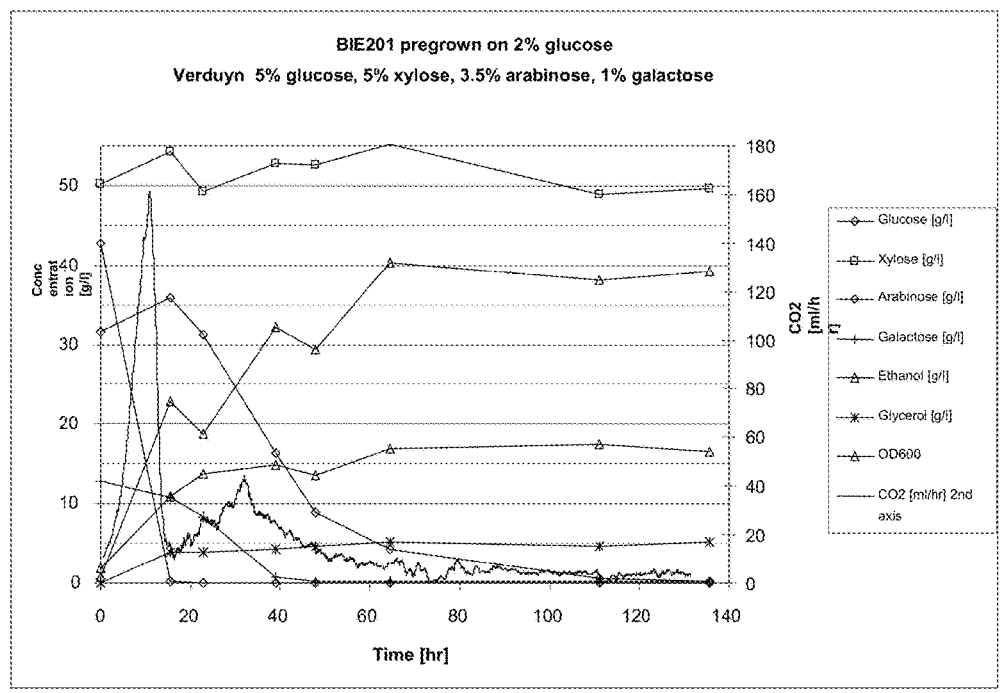
FIG. 12 sets out sugar conversion and product formation of BIE201 on synthetic corn fiber model medium. CO2 production was measured constantly. Growth was monitored by following optical density of the culture. Preculture was grown on 2% glucose.

The experiments clearly show that reference strain BIE104 converted glucose rapidly, but was not able to convert neither arabinose nor galactose within 140 hours (FIG. 10). However, strain BIE104A2P1c and BIE201 were capable to convert arabinose and galactose (FIGS. 11 and 12, respectively). Galactose and arabinose utilization started immediately after glucose depletion after less than 20 hours. Both sugars were converted simultaneously. However, strain BIE201 which was improved for arabinose growth under anaerobic conditions, consumed both sugars more rapidly (FIG. 12). In all fermentations only glycerol was generated as by-product. The data of the fermentation of BIE201 are given herein in table 2.

TABLE 2

Sugar concentrations and ethanol concentrations (g/l) of BIE201 fermentation as shown in FIG. 12. Maximal ethanol concentration is calculated by multiplying concentrations by 0.51 for each sugar and summarizing. Ethanol concentration at 136 h (39.2 g/l) means an ethanol yield of 0.45 ethanol/g sugar. This yield shows that all sugars were converted to ethanol.
Concentrations in g/l

| Time (h) | Glu | Xyl | Ara | Gal | EtOH |
|---|---|---|---|---|---|
| 0 | 42.8 | 50.2 | 31.6 | 12.9 | 0.7 |
| 16 | 0.1 | 54.2 | 35.8 | 10.8 | 22.9 |
| 23 | 0.0 | 49.2 | 31.3 | 8.4 | 18.7 |
| 39 | 0.1 | 52.8 | 16.3 | 0.7 | 32.1 |
| 48 | 0.0 | 52.5 | 8.9 | 0.2 | 29.4 |
| 65 | 0.0 | 55.1 | 4.3 | 0.3 | 40.3 |
| 111 | 0.0 | 48.8 | 0.5 | 0.3 | 38.1 |
| 136 | 0.0 | 49.6 | 0.2 | 0.3 | 39.2 |

Maximal ethanol concentrations (in g/l) from
Glucose 21.8
Arabinose 16.1
Galactose 6.6
Total 44.5
Experimental ethanol yield 0.45 g ethanol/g sugar From this calculation it is clear that the sugars glucose, galactose and arabinose are each converted into ethanol.

Example 4

Effect of the PPP-Genes on Sugar Conversion

To test the effect of the PPP-genes on sugar conversion, single colonies from strain BIE104A2 and BIE105A2 were inoculated in YNB-medium (Difco) supplemented with 2% glucose. Both strains contain the arabinose-genes and were evolved for growth on arabinose (as described in example 2, section 2.1). Strain BIE105A2 has the background of an industrial strain. However, it was transformed with the same methods and constructs as described before (example 1, section 1.2).

Precultures were harvested and inoculated in synthetic corn fiber model medium (Verduyn et al., Yeast 8:501-517, 1992; 5% glucose, 5% xylose, 3.5% arabinose, 1.5% galactose) with a starting OD 600 of approximately 2 in the BAM. CO2 production was monitored constantly. Sugar conversion and product formation was analyzed by NMR. The data represent the residual amount of sugars at the indicated (glucose, arabinose, galactose and xylose in grams per liter) and the formation of (by-)products (ethanol, glycerol). Growth was monitored by following optical density of the culture at 600 nm. The experiment was running for approximately 160 hours.

Figure 13:
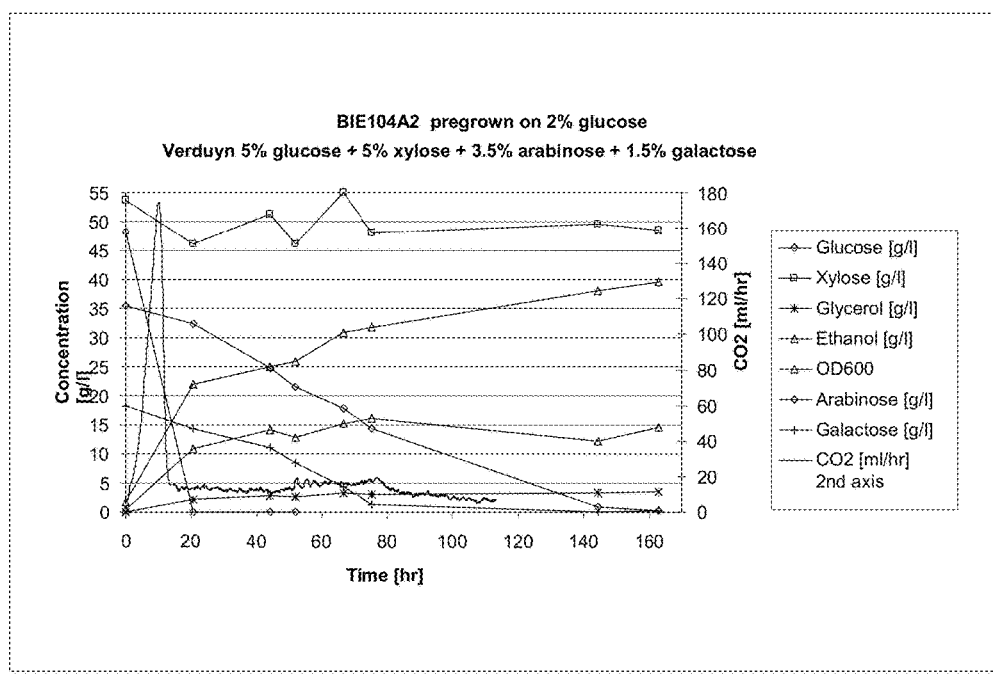
FIG. 13 sets out sugar conversion and product formation of BIE104A2 on synthetic corn fiber model medium. CO2 production was measured constantly. Growth was monitored by following optical density of the culture. Preculture was grown on 2% glucose.

The experiments show that both strains are capable to convert arabinose and galactose immediately after glucose depletion without the overexpression of the PPP-genes (FIGS. 13 and 14).

Example 5

Introduction of Constitutively Expressed Genes Encoding Xylose Isomerase and Xylulokinase 5.1 Yeast Transformation Strain BIE104A2P1 (MATa URA3 HIS3 LEU2 TRP1 MAL2-8 SUC2 SIT2::[TDH3-araA, ENO1-araB, PGI1-araD] ΔGRE3::[TPI1p-TAL1, ADH1p-TKL1, PGI1p-RPE1, ENO1p-RKI1]) was transformed with plasmid pPWT042 (FIG. 16). Plasmid pPWT042 derives from vector pPWT007 (FIG. 15). It contains the codon pair optimized xylulokinase from *S. cerevisiae* and the codon-pair optimized xylose isomerase from *Bacteroides uniformis* (SEQ 2) as disclosed in patent application PCT/EP2009/52623. Prior to the transformation of BIE104A2P1, pPWT042 was linearized using the restriction enzyme SfiI, according to the instructions provided by the supplier. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

Upon digestion of plasmid pPWT042 with SfiI, its integration is directed to the SIT4-locus (Gottlin-Ninfa and Kaback (1986) Molecular and Cellular Biology Vol. 6, No. 6, 2185-2197) in the genome (FIG. 17). Transformants were characterized using PCR and Southernblotting techniques, as described in example 1 (section 1.2).

A strain with one copy of plasmid pPWT042 integrated into the genome was designated BIE104A2P1Y9.

5.2 Growth Experiments

Single colony isolates of strains BIE104A2P1Y9 were used to inoculate YNB-medium (Difco) supplemented with 2% glucose or 2% galactose. The inoculated flasks were incubated at 30° C. and 280 rpm until the optical density at 600 nm reached a value of at least 2.0.

YNB-medium supplemented with 1% arabinose and 1% xylose was inoculated with the overnight cultures at a starting OD600 of 0.2. Cells were grown at 30° C. and 280 rpm. The optical density at 600 nm was monitored regularly. When the optical density reached a value larger than 2.0, an aliquot of the culture was transferred to fresh YNB medium containing 2% xylose and 0.2% arabinose. The amount of cells added was such that the starting OD600 of the culture was 0.2.

The optical density was monitored regularly. The results are shown in FIG. 18, panel a (precultures on galactose) and panel b (precultures on glucose).

The results clearly show that the strains are capable of utilizing glucose, galactose, arabinose and xylose.

5.3 Marker Rescue

To remove the selection marker introduced by the integration of plasmid pPWT042, the strain BIE104A2P1Y9 was cultured in YPD-medium, starting from a colony isolate. 25 μl of an overnight culture was used to inoculate fresh YPD-medium. After serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Fluoro-acetamide resistant colonies were subjected to PCR analysis and, in case of correct PCR-profiles, Southern blot analysis (section 1.3, example 1). One of the strains that showed the correct pattern of bands on the Southern blot is the strain designated as BIE104A2P1X9.

5.4 Growth Experiments

Single colony isolates of strain BIE104A2P1X9 (BIE104A2P1×9a1 and BIE104A2P1×9a2) were used to inoculate Verduyn-medium (Difco) supplemented with 2% glucose. The inoculated flasks were incubated at 30° C. and 280 rpm for approximately 24 hours.

Verduyn-medium supplemented with 2% xylose was inoculated with the overnight cultures at a starting OD600 of 0.2. Cells were grown at 30° C. and 280 rpm. The optical density at 600 nm was monitored regularly. The results are shown in FIG. 19.

The results clearly show that both independent colonies of strain BIE104A2P1X9 are still capable to utilize xylose after marker rescue. As was already shown in example 3, the strain is capable to utilize glucose, arabinose and galactose (FIG. 11 and FIG. 12).

Example 6

Transformation of *S. cerevisiae* for Succinic Acid Production on Arabinose and Galactose 6.1. Expression Constructs Expression construct pGBS414PPK-3 comprising a phosphoenol pyruvate carboxykinase PCKa (E.C. 4.1.1.49) from *Actinobacillus succinogenes*, and glycosomal fumarate reductase FRDg (E.C. 1.3.1.6) from *Trypanosoma brucei*, and an expression construct pGBS415FUM3 comprising a fumarase (E.C. 4.2.1.2.) from *Rhizopus oryzae*, and a peroxisomal malate dehydrogenase MDH3 (E.C. 1.1.1.37) are made as described previously in WO2009/065778 on p. 19-20, and 22-30 which herein enclosed by reference including the figures and sequence listing.

Expression construct pGBS416ARAABD comprising the genes araA, araB and araD, derived from *Lactobacillus plantarum*, are constructed by cloning a PCR product, comprising the araABD expression cassette from plasmid pPWT018, into plasmid pRS416. The PCR fragment is generated using Phusion® DNA polymerase (Finnzymes) and PCR primers defined in here as SEQ ID 22 and SEQ ID 23. The PCR product is cut with the restriction enzymes SalI and NotI, as is plasmid pRS416. After ligation and transformation of *E. coli* TOP10, the right recombinants are selected on basis of restriction enzyme analysis. The physical map of plasmid pGBS416ARAABD is set out in FIG. 20

6.2. *S. cerevisiae* Strains

The plasmids pGBS414PPK-3, pGBS415-FUM-3 are transformed into *S. cerevisiae* strain CEN.PK113-6B (MATA ura3-52 leu2-112 trp1-289). In addition plasmid pGBS416ARAABD is transformed into this yeast to create prototrophic yeast strains. The expression vectors are transformed into yeast by electroporation. The transformation mixtures are plated on Yeast Nitrogen Base (YNB) w/o AA (Difco)+2% glucose.

Strains are subjected to adapted evolution (see section 2) for growth on arabinose as sole carbon source.

6.3. Growth Experiments and Succinic Acid Production

Transformants are inoculated in 20 ml pre-culture medium consisting of Verduyn medium (Verduyn et al., 1992, Yeast. July; 8(7):501-17) comprising 2% galactose (w/v) and grown under aerobic conditions in 100 ml shake flasks in a shaking incubator at 30° C. at 250 rpm. After approximately 24 hours, cells are transferred to fresh Verduyn medium containing either 2% glucose, 2% galactose or 2% arabinose, or mixtures thereof, in fourfold. Two flasks are incubated under aerobic conditions, two flasks are incubated under anaerobic conditions, for instance by closing the flasks using a waterlock or by incubation in an anaerobic orbital shaker. At time intervals, culture samples are taken. The samples are centrifuged for 5 minutes at 4750 rpm. 1 ml supernatant is used to measure succinic acid levels by HPLC as described in section 6.4.

6.4. HPLC Analysis

HPLC is performed for the determination of organic acids and sugars in. The principle of the separation on a Phenomenex Rezex-RHM-Monosaccharide column is based on size exclusion, ion-exclusion and ion-exchange using reversed phase mechanisms. Detection takes place by differential refractive index and ultra violet detectors.

LITERATURE

| Lit. No | Source |
|---|---|
| (1) | Bioresource Technology 1994 Vol. 47 page 283-284 |
| (2) | Micard, Enzyme Microbiol Technology 1996 Vol 19 page 163-170 |
| (3) | DOE Radke, Idaho wheat straw composition |
| (4) | Grohman and Botast Process Biochemistry 1997 Vol. 32 No 5 405-415 |
| (5) | Saska B&B 1995 517-523 |
| (6) | PCT/EP2009/52623 |
| (7) | Zheng Appl. Biochem. Microbiol. 2007, Vol. 136-140 pp 423-436 |
| (8) | Bradshaw Appl Biochem. Microbiol. 2007 Vol 136-140 page 395-406 |
| (9) | Cara Appl Biochem. Microbiol. 2007 Vol 136-140 page 379-394 |

The invention claimed is:

1. A process for the production of at least one fermentation product from a sugar composition comprising glucose, galactose and arabinose, said process comprising:
   a) fermenting said sugar composition in the presence of a yeast recombinant belonging to the genera *Saccharomyces, Kluyveromyces, Candida, Pichia, Schizosaccharomyces, Hansenula, Kloeckera, Schwanniomyces* and/or *Yarrowia*, and
   b) recovering the fermentation product,
   wherein said recombinant yeast comprises gene araA, araB and araD,
   wherein each of said glucose, galactose and arabinose is converted into at least one fermentation product, and
   wherein said at least one fermentation product is selected from the group consisting of: ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, 1,3-propane-diol, ethylene, glycerol, a β-lactam antibiotic, a cephalosporin, and vitamins.

2. The process according to claim 1, wherein said fermentation product comprises ethanol.

3. The process according to claim 1, wherein said sugar composition is produced from lignocellulosic material by:
 a) pretreatment of at least one lignocellulosic material to produce pretreated lignocellulosic material;
 b) enzymatic treatment of the pretreated lignocellulosic material to produce said sugar composition.

4. The process according to claim 1, wherein said yeast belongs to the genus *Saccharomyces*.

5. The process according to claim 4, wherein said yeast is a-*Saccharomyces cerevisiae*.

6. The process according to claim 1, wherein said yeast comprises a deletion of an aldose reductase gene.

7. The process according to claim 6, wherein said yeast comprises xylA-gene and/or XKS1-gene.

8. The process according to claim 7, wherein said genes are introduced in said yeast by introduction into a host cell a nucleic acid construct comprising:
 a) a cluster comprising PPP gene TAL1, TKL1, RPE1 and/or RKI1, under control of strong promoters,
 b) a cluster comprising a xylA-gene and/or XKS1-gene under control of constitutive promoter,
 c) a cluster comprising gene araA, araB and araD and/or a cluster of xylA-gene and/or XKS1-gene; and
 d) deletion of an aldose reductase gene;
 and adaptive evolution of said yeast.

9. The process according to claim 8, wherein said host cell is an inhibitor tolerant cell.

10. The process according to claim 8, wherein said host cell is an industrial strain.

11. The process according to claim 1, wherein fermentation is conducted under anaerobic and/or oxygen limited conditions.

12. The process according to claim 1, wherein said amino acid is selected from the group consisting of lysine, methionine, tryptophan, threonine, and aspartic acid.

* * * * *